(12) United States Patent
Mauger et al.

(10) Patent No.: US 9,314,624 B2
(45) Date of Patent: Apr. 19, 2016

(54) SYSTEMS AND METHODS FOR ALTERING THE INPUT DYNAMIC RANGE OF AN AUDITORY DEVICE

(71) Applicant: Cochlear Limited, Macquarie University (AU)

(72) Inventors: Stefan J. Mauger, Rosanna (AU); John M. Heasman, South Melbourne (AU); Martin E. G. Hillbratt, Lindome (SE)

(73) Assignee: Cochlear Limited, Macquarie University, NSW (AU)

( * ) Notice: Subject to any disclaimer, the term of this patent is extended or adjusted under 35 U.S.C. 154(b) by 443 days.

(21) Appl. No.: 13/744,228

(22) Filed: Jan. 17, 2013

(65) Prior Publication Data
US 2014/0198922 A1    Jul. 17, 2014

(51) Int. Cl.
*H04R 25/00* (2006.01)
*A61N 1/36* (2006.01)

(52) U.S. Cl.
CPC ............ *A61N 1/36032* (2013.01); *H04R 25/00* (2013.01); *H04R 25/407* (2013.01); *H04R 2225/43* (2013.01)

(58) Field of Classification Search
CPC .. H04R 25/00; H04R 25/407; H04R 2225/43; A61N 1/36032
See application file for complete search history.

(56) References Cited

U.S. PATENT DOCUMENTS

| 5,907,622 | A | 5/1999 | Dougherty |
| 7,010,133 | B2 | 3/2006 | Chalupper et al. |
| 7,372,969 | B2 | 5/2008 | Roeck |
| 2002/0057791 | A1* | 5/2002 | Piket ...................... H04B 3/234 379/417 |
| 2007/0019833 | A1 | 1/2007 | Barthel |
| 2010/0316240 | A1* | 12/2010 | Semcken ............ H04M 1/2475 381/331 |
| 2011/0135129 | A1* | 6/2011 | Neal .............................. 381/320 |
| 2012/0076311 | A1* | 3/2012 | Isabelle et al. ................... 381/57 |
| 2012/0076312 | A1* | 3/2012 | Iyengar ........................... 381/57 |

FOREIGN PATENT DOCUMENTS

DE    102005034647    2/2007

OTHER PUBLICATIONS

Rainer Martin, Noise Power Spectral Density Estimation Based on Optimal Smoothing and Minimum Statistics, IEEE Transactions on Speech and Audio Processing, Jul. 5, 2001, pp. 504-512, vol. 9, No. 5.
Pam Dawson et al., Clinical Evaluation of Signal-to-Noise Ratio-Based Noise Reduction in Nucleus Cochlear Implant Recipients, Ear & Hearing, 2011, pp. 1-9, vol. 32, No. 2, Lippincott Williams & Wilkins.

(Continued)

*Primary Examiner* — Tuan D Nguyen

(57) ABSTRACT

An auditory device according to one embodiment includes a processing unit configurable to determine a noise estimate and a measure for one of a plurality of samples of an audio signal. The measure relates to an upper volume bounds. The processing unit is configured to apply at least one rule using the noise estimate and/or the measure to identify an input dynamic range for mapping the audio signal to a corresponding stimulation signal.

34 Claims, 9 Drawing Sheets

(56) References Cited

OTHER PUBLICATIONS

Chris J. James et al., Adaptive Dynamic Range Optimization for Cochlear Implants: A Preliminary Study, Ear & Hearing, Feb. 2002, pp. 49S-58S, Lippincott Williams & Wilkins.

Israel Cohen, Noise Spectrum Estimation in Adverse Environments: Improved Minima Controlled Recursive Averaging, IEEE Transactions on Speech and Audio Processing, Sep. 5, 2003, pp. 466-475, vol. 11, No. 5.

* cited by examiner

SYSTEMS AND METHODS FOR ALTERING THE INPUT DYNAMIC RANGE OF AN AUDITORY DEVICE

BACKGROUND

Various types of auditory devices provide persons with different types of hearing loss with the ability to perceive sound or perceive improved sound, or persons having normal hearing to experience different sound perception (e.g. with less noise). Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea, where sound vibrations are converted into neural signals, or any other part of the ear, auditory nerve, or brain that may process or convey the neural signals.

Persons with some forms of conductive hearing loss may benefit from auditory devices such as acoustic hearing aids or vibration-based auditory devices. An acoustic hearing aid typically includes a small microphone to detect sound, an amplifier to amplify certain portions of the detected sound, and a small speaker to transmit the amplified sounds into the person's ear. Vibration-based auditory devices typically include a small microphone to detect sound and a vibration mechanism to apply vibrations corresponding to the detected sound directly or indirectly to a person's bone or teeth, for example, thereby causing vibrations in the person's inner ear and bypassing the person's auditory canal and middle ear. Vibration-based auditory devices include, for example, bone-anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based auditory devices may use similar vibration mechanisms to transmit sound via direct or indirect vibration of teeth or other cranial or facial bones or structures.

Persons with severe to profound sensorineural hearing loss may benefit from surgically implanted auditory devices (prostheses), such as cochlear implants, auditory brainstem implants, or auditory midbrain implants. For example, a cochlear implant can provide a person having sensorineural hearing loss with the ability to perceive sound by stimulating the person's auditory nerve via an array of electrodes implanted within the cochlea. A component of the cochlear implant detects sound waves, which are converted into a series of electrical stimulation signals that are delivered to the person's cochlea via the array of electrodes. Auditory brainstem implants can use technology similar to cochlear implants, but instead of applying electrical stimulation to a person's cochlea, auditory brainstem implants apply electrical stimulation directly to a person's brainstem, bypassing the cochlea altogether. Electrically stimulating auditory nerves in a cochlea with a cochlear implant or electrically stimulating a brainstem may enable persons with sensorineural hearing loss to perceive sound.

Further, some persons may benefit from auditory devices that combine one or more characteristics of acoustic hearing aids, vibration-based auditory devices, cochlear implants, and auditory brainstem implants to enable the person to perceive sound. Such auditory devices can be referred to generally as hybrid auditory devices.

Common among some or all the above-described auditory devices is the need to determine the stimulus to provide to the auditory devices' stimulation mechanism/device (electrode, vibrator, speaker, etc.), so that the user of the auditory device is able to hear important sounds (information) at a loudness that is perceptible, yet comfortable for the user. This requires, first, that the auditory device be properly fit to the user, so that one or more stimulation channels, for example, provide appropriate maximum and minimum levels of stimulation to the user. For example, an acoustic hearing aid should be fit so that the hearing aid's speaker preferably does not cause discomfort to the user in the presence of loud ambient sounds, but still allows the user to hear quiet ambient sounds. For electrical, rather than acoustic stimulation, fitting typically refers to choosing an acceptable range of current levels to be provided to one or more stimulation electrodes, or a stimulus signal to be provided to a vibration mechanism or other source of stimulation.

In addition to fitting, how the auditory device initially handles the incoming ambient sounds may also be important. Noise reduction techniques are commonly employed in auditory devices to attenuate parts of the signal that are determined to be noise, while retaining the target information content of the signal. Compression and expansion techniques are also commonly employed in auditory devices to amplify or attenuate signals that are too soft or too loud to improve listening comfort and speech understanding.

While noise reduction can decrease the loudness of masking noise, it can also, to a lesser extent, decrease the loudness of the target talker. It also has no inherent limits, so in very noisy environments typical noise reduction schemes remove much of the noise signal, which reduces listening quality. While compression and expansion systems can improve listening comfort in loud or soft environments, they can also have negative effects on listening quality. For example, in the case of compressors that attenuate short, loud sounds, they may also attenuate the background during and after the short loud sound creating the perception of a transient pumping noise, which reduces listening quality.

Thus, even if an auditory device is properly fit to its user and includes some form of noise reduction and compression and expansion algorithms, listening in noisy or loud or soft environments can result in relatively poorer speech quality and intelligibility when listening in real-world environments.

SUMMARY

Aspects of the present disclosure relate generally to sound processing and, more particularly, to improving the listening experience for a user of an auditory device. Generally, many typical auditory devices operate with a fixed input dynamic range and utilize complicated multi-stage signal paths, making it difficult to predict system effects caused by changing a single amplitude-modifying element. Furthermore, the combination of multiple algorithms, each modifying gains applied to the incoming signal, may behave in an unpredictable manner when operating together in unison. The result may be a poorer performance or sound quality under some real-world listening environments.

The present disclosure relates to one or more aspects intended to improve on prior multi-stage processing strategies. Generally, an auditory device incorporating aspects set forth herein includes a processor to adjust an input dynamic range based on a noise estimate and/or a measure, such as a percentile estimate of the input audio signal. For example, the percentile estimate could represent the ninetieth percentile input signal amplitude over a preceding time period, such as thirty seconds. The processor uses the noise estimate and/or measure, which may be in units of decibels (dB) of Sound Pressure Level (SPL), for example, to set the input dynamic range. In this way, the input dynamic range adjusts to fit the listening environment. The adjustments are preferably smoothed over a suitable time period, such as thirty seconds, to allow the user of the device to adapt. One or more rules may be applied to ensure that the dynamic range is not set too broad or narrow, or too low or high. In addition, one or more break rules may be applied to allow the device to quickly respond to sounds louder than a particular amplitude, such as those at a certain percentage above the measure. The user's own voice, often louder than the far field target information, might trigger such a break rule, for example. The result is an improved listening experience for the user, where important information, such as a target speaker's voice, is more readily heard, while noise is advantageously suppressed.

More specifically, in accordance with one embodiment, an auditory device includes a processing unit configurable to determine a noise estimate and a measure for one of a plurality of samples of an audio signal, such as an input audio signal. The processing unit applies at least one rule using the noise estimate and/or the measure to identify an input dynamic range for mapping the input audio signal to a corresponding stimulation signal. The auditory device may further include a front end configurable to generate the plurality of samples and a stimulation unit for providing a stimulus based on the stimulation signal to a user of the auditory device. The stimulus may be an electrical stimulus or a mechanical stimulus, for example.

In a further embodiment, the processing unit is further configurable to determine respective noise estimates and measure for other of the plurality of samples and to temporally smooth a plurality of the noise estimates and measures while identifying the input dynamic range. Alternatively, the processing unit is further configurable to determine respective noise estimates and measures for other of the plurality of samples, to identify a plurality of input dynamic ranges based on the determined respective noise estimates and measures, and to temporally smooth the identified plurality of input dynamic ranges for mapping the audio signal to a corresponding stimulation signal.

The at least one rule may include an information rule, a noise rule, or both, for example. The information rule includes determining whether an upper value of the input dynamic range is greater than an upper value maximum limit and whether the upper value of the input dynamic range is less than an upper value minimum limit. Upon determining that the upper value of the input dynamic range is greater than the upper value maximum limit or less than the upper value minimum limit, the information rule includes adjusts the upper value respectively to the upper value maximum limit or the upper value minimum limit.

The noise rule includes determining whether a lower value of the input dynamic range is less than a lower value minimum limit and whether the lower value of the input dynamic range is greater than a lower value maximum limit. Upon determining that the lower value of the input dynamic range is less than the lower value minimum limit or greater than the lower value maximum limit, the noise rule calls for adjusting the lower value respectively to the lower value minimum limit or the lower value maximum limit.

The at least one rule to be applied could additionally or alternatively include a stretch rule, a squash rule, or both. The stretch rule includes determining whether a difference between the upper value and the lower value is greater than a maximum difference threshold. If so, the stretch rule adjusts at least one of the upper value and the lower value so that the difference is not greater than the maximum difference threshold.

The squash rule includes determining whether the difference between the upper value and the lower value is less than a minimum difference threshold. If so, the squash rule adjusts at least one of the upper value and the lower value so that the difference is not less than the minimum difference threshold.

The auditory device can further include at least one user input to set at least one of a volume and a sensitivity. The volume is used in determining an upper value of the input or output dynamic range, while the sensitivity is used in determining a lower value of the input or output dynamic range.

According to this first embodiment, the processing unit maps the input audio signal to the corresponding stimulation signal according to a map using the lower value of the input dynamic range and an upper value of the input dynamic range. The input dynamic range maps to a corresponding output range predetermined for the user and the stimulation device. For electrical stimulation, the mapping may include determining a signal amplitude, a pulse width, or an inter-phase gap for the stimulation signal, or some combination of these, for example. For acoustic or vibratory stimulation, the mapping may include a speaker volume or vibration rate or amplitude, for example.

The at least one rule could further comprise a break rule, in which the processor could additionally determine whether a magnitude of the input audio signal exceeds an upper value of the input dynamic range by a break threshold. If it does, the processor could increase the upper value of the input dynamic range.

In accordance with a second embodiment, a method for processing an audio signal, such as an input audio signal, comprises determining an amplitude data, setting an input dynamic CSPL (comfort sound pressure level) parameter based on the amplitude data, setting an input dynamic TSPL (threshold sound pressure level) parameter, and mapping the audio signal to a stimulation signal corresponding to the audio signal, where the mapping is, at least in part, according to the input dynamic CSPL parameter and the input dynamic TSPL parameter. In one example, the amplitude data is a measure of a characteristic of an average peak amplitude of the audio signal. The method may further include providing a stimulation according to the stimulation signal.

The method may further include performing at least one of the following determinations and adjustments: (a) determining whether the input dynamic CSPL parameter is greater than an upper value maximum limit, and if so, adjusting the input dynamic CSPL parameter to no more than the upper value maximum limit; (b) determining whether the input dynamic CSPL parameter is less than an upper value minimum limit, and if so, adjusting the input dynamic CSPL parameter to no less than the upper value minimum limit; (c) determining whether the input dynamic TSPL parameter is greater than a lower value maximum limit, and if so, adjusting the input dynamic TSPL parameter to no more than the lower value maximum limit; (d) determining whether the input dynamic TSPL parameter is less than a lower value minimum limit, and if so, adjusting the input dynamic TSPL parameter to no less than the lower value minimum limit; (e) determining whether a difference between the input dynamic CSPL parameter and the input dynamic TSPL parameter is greater than a maximum difference threshold, and if so, adjusting at least one of the input dynamic CSPL parameter and the input dynamic TSPL parameter so that the difference is not greater than the maximum difference threshold; and (f) determining whether the difference between the input dynamic CSPL parameter and the input dynamic TSPL parameter is less than a minimum difference threshold, and if so, adjusting at least one of the input dynamic CSPL parameter and the input dynamic TSPL parameter so that the difference is not less than the minimum difference threshold.

The method may yet further include determining whether a magnitude of the audio signal exceeds the input dynamic CSPL parameter by a break threshold, and if so, increasing the input dynamic CSPL parameter.

The stimulation signal may, for example, be an electrical stimulation signal characterized by a C-Level current level and a T-Level current level, where the input dynamic CSPL parameter is mapped to the C-Level current level, the input dynamic TSPL parameter is mapped to the T-Level current level, and both the C-Level current level and the T-Level current level are predetermined. The mapping may include determining a signal amplitude, a pulse width, and/or an interphase gap for the stimulation. Alternatively or additionally, the mapping may include determining a stimulus level according to one or more of a stimulus level, a current level, a pulse width, a vibration rate, and an interphase gap.

Setting the input dynamic TSPL parameter may further include determining a noise-level estimate during a noise smoothing time period, and setting the input dynamic TSPL parameter to the noise-level estimate.

A method according to a third embodiment includes determining a measure and a noise estimate for an audio signal, adjusting an input dynamic range based on the measure and the noise estimate, and determining an output representative of a stimulus level based on the measure, the noise estimate, and a static input. In one example, the audio signal is an input signal composed of a plurality of samples, and the adjusting is performed for one of the plurality of samples. In another example, the audio signal is a channelized input audio signal and the method includes determining a measure and a noise estimate, adjusting an input dynamic range, and determining an output for each channel in the channelized signal. Determining the output may additionally include applying at least one user input corresponding to volume or sensitivity, where the user inputs are received asynchronously. Alternatively or additionally, the static input includes a device-specific parameter and/or a user-specific parameter. As other examples, the static input includes a minimum sound pressure level corresponding to a noise floor, a maximum sound pressure level corresponding to a maximum value of an analog-to-digital conversion, and a T-Level and C-Level corresponding respectively to a minimum and maximum of an electrical dynamic range of an acoustic-to-electric mapping function determined using at least the measure, the noise estimate, and/or the static input. The method further preferably includes adjusting an acoustic-to-electric mapping function based on the measure and the noise estimate, where determining the output includes applying the acoustic-to-electric mapping function to the audio signal. The method may further include communicating the output to a stimulation device, such as by applying an acoustic-to-electric mapping function to the input signal.

Yet another embodiment provides a method for processing an audio signal in an auditory device having first processing unit associate with a first device and a second processing unit associated with a second device. The auditory device may be a bilateral auditory device, for example. The method includes determining, at the first processing unit, an input dynamic range based, at least in part, on a communication received from the second processing unit. The communication is associated with the second device and includes a dynamic TSPL, a dynamic smoothed TSPL, a dynamic CSPL, a dynamic smoothed CSPL, a break rule output, a scaling value input, a volume input, a sensitivity input, and/or a Q-Value input. The method further includes determining, at the first processing unit, an output representative of a stimulus level for the first device, based on the determined input dynamic range. The method may further include the first processing unit communicating the determined input dynamic range to the second processing unit.

The above and additional aspects, examples, and embodiments are further described in the present disclosure.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure.

Various embodiments of the present disclosure may be implemented in conjunction with a variety of auditory devices commercially available today or as may be developed in the future. For example, the auditory devices may include prosthetic hearing devices, as well as acoustic devices for the outer, middle, and inner ear, and others. Thus, cochlear implants, including totally implantable cochlear implants, bone conduction devices, direct acoustic stimulation devices, auditory brain stem implants, middle ear implants, and/or other auditory devices are contemplated by the present disclosure. Further, many features and functions disclosed herein may be equally applicable to devices other than prosthetic hearing devices, including other types of medical and non-medical devices. In addition, various embodiments of the present disclosure are applicable to both unilateral and bilateral auditory devices (and others). However, for ease of illustration, embodiments are described herein in conjunction with auditory devices, and in particular, with a unilateral cochlear implant device.

Generally, embodiments described herein are directed to altering an input dynamic range (i.e. dynamically changing the CSPL and/or TSPL) during operation or use of an auditory device to help ensure that the most important part of an input audio signal is used for stimulation. At a high level, this dynamic CSPL and dynamic TSPL concept is achieved by mapping an upper portion (e.g. a $95^{th}$ percentile estimate) of the input audio signal to a C-Level (upper portion of the dynamic range perceived as loud) and by mapping a lower portion (e.g. a noise estimate) to a T-Level (lower portion of the dynamic range perceived as soft).

Figure 1A:
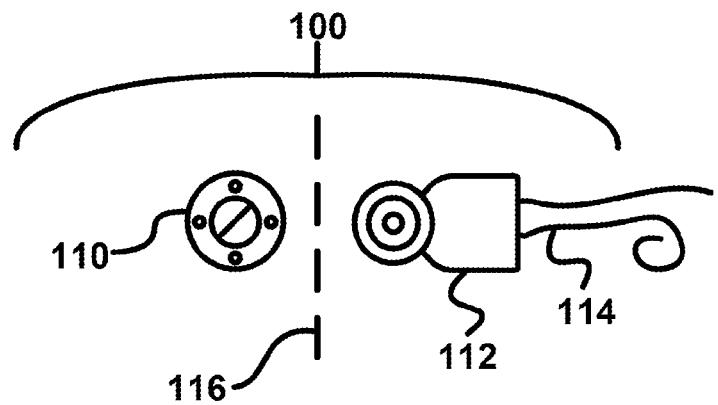
FIG. 1A is a schematic block diagram illustrating an auditory device.

FIG. 1A is a schematic block diagram illustrating an auditory device 100 in the form of a cochlear implant. The auditory device 100 includes a processing unit 110 and an implanted unit 112. The implanted unit 112 is implanted in a portion of a skull of a user under their skin 116. In an example in which the auditory device 100 is a totally implantable hearing prosthesis, the processing unit 110 is also implanted in the user's skull and below the user's skin 116. Additionally, an enclosure may house the processing unit 110 and the implanted unit 112.

The implanted unit 112 includes an electrode array 114 implanted in the user's cochlea. Each electrode on the electrode array 114 stimulates a portion of the cochlea that allows the user to perceive sound having a range of frequencies. The electrodes in the electrode array 114 deliver electrical stimuli to one or more portions of the user's cochlea to allow the user to perceive at least a portion of a sound.

Figure 1B:
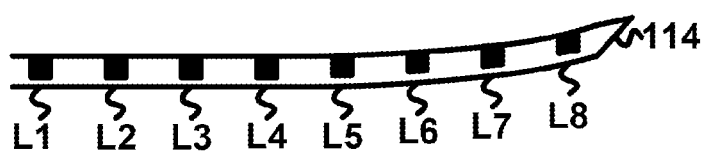
FIG. 1B is a schematic diagram illustrating an electrode array for the auditory device of FIG. 1A.

FIG. 1B illustrates the electrode array 114, which includes electrodes L1-L8. The electrode array 114 may include more or fewer electrodes. For instance, the electrode array 114 may include twenty-two electrodes. To facilitate implantation, the electrode array 114 is made of a flexible material suitable for being implanted in the user's cochlea. When an electrode, such as electrode L8, delivers an electrical stimulus, the user perceives a sound having a particular frequency (e.g. about 1500 Hz).

The volume of the sound perceived by the user of the auditory device 100 depends on the stimulus current of each electrode provided by the processing unit 112 upon receiving a sound. The stimulus currents are the currents of the electrical stimuli delivered by one or more of the electrodes L1-L8. In general, as the current of a stimulus increases, the loudness of the sound perceived by the user increases. A value of a stimulus current depends on a sound pressure level (SPL) of a sound received by the processing unit 110.

Figure 1C:
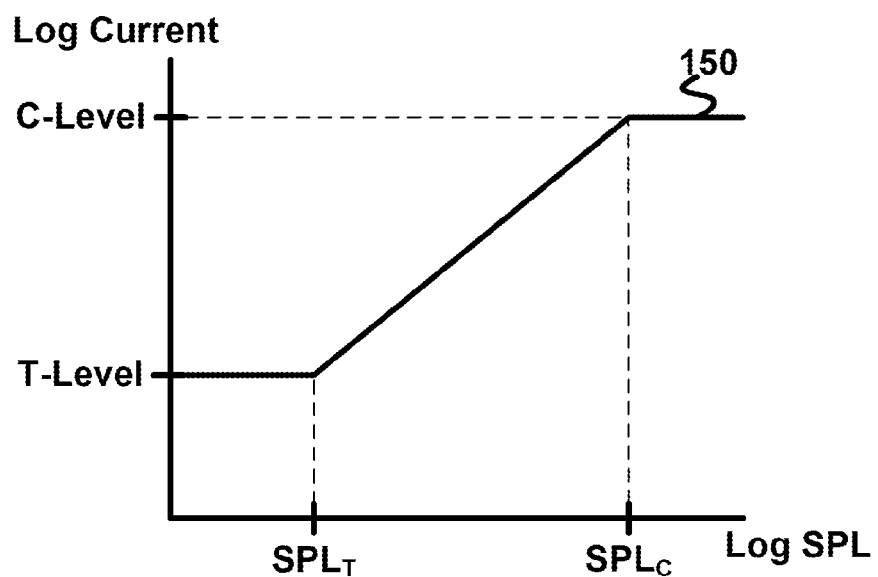
FIG. 1C is a conceptual illustration of a dynamic range curve mapping between acoustic signal loudness and electrode array current level (dB).

FIG. 1C is a conceptual illustration of a dynamic range curve 150 of an electrode on the electrode array 114. The dynamic range curve 150 is plotted on a log-linear scale, with the x-axis representing a logarithm of the SPL of a sound, and the y-axis representing the stimulus current in linear units. The stimulus current is expressed in any unit suitable for use in the auditory device 100. In one example, the unit is microamperes. In another example, the unit is any unit capable of being converted to microamperes.

The dynamic range for the electrical stimuli from an electrode is a difference between a threshold level (T-Level) and a maximum comfort level (C-Level). A T-Level for an electrode corresponds to a stimulus current that results in the user just being able to hear a sound at a given frequency. In other words, the T-Level is typically the stimulus current below which the user is not able to perceive the sound. The C-Level for an electrode typically corresponds to the stimulus current applied by the electrode to the user's cochlea that results in a sound with a certain pitch percept that the user can perceive comfortably. That is, the C-Level is the stimulus current above which the user perceives the sound as being uncomfortably loud.

The SPL of the sound at the acoustic threshold level is identified as the output TSPL, and the SPL of the sound at the acoustic comfort level is identified as output CSPL. Output TSPL represents the SPL of the sound below which amplification is needed to allow the user to perceive the sound. Similarly, output CSPL represents the SPL of the sound above which the sound becomes uncomfortably loud. Between output TSPL and output CSPL, the log outputs increase approximately linearly with the log-SPL inputs.

For a sound having an SPL that is less than the dynamic TSPL, the sound will be mapped to below the T-Level, and not perceived. For a sound having an SPL that is between the dynamic TSPL and the dynamic CSPL, the stimulus current varies approximately linearly with the SPL (dB) of the sound. The slope of the dynamic range curve 150 may have some additional curvature due to the Q-Factor (see, e.g., description accompanying FIGS. 4 and 5). In one example, the slope of the dynamic range curve 150 is adjustable, allowing the dynamic range curve 150 to be customized to the user. For a sound having an SPL greater than the output CSPL (or C-Level), the stimulus current is typically fixed at the C-Level. In other words, the output CSPL is the saturation level for the electrode. In accordance with various embodiments described herein, adaptive adjustments are made to the dynamic TSPL and/or dynamic CSPL during operation of the auditory device.

Each of the electrodes L1-L8 has a dynamic range curve. While different users of hearing prostheses like the auditory device 100 may have similar types of hearing losses (e.g., sensorineural hearing loss), each user may have a unique sensitivity to sounds at different frequencies. To accommodate the user's specific hearing loss, the auditory device 100 is fit to the user of the auditory device 100 using a computing device having a wired or wireless connection. Fitting the auditory device 100 to the user includes determining the dynamic range for each of the electrodes L1-L8.

Figure 2:
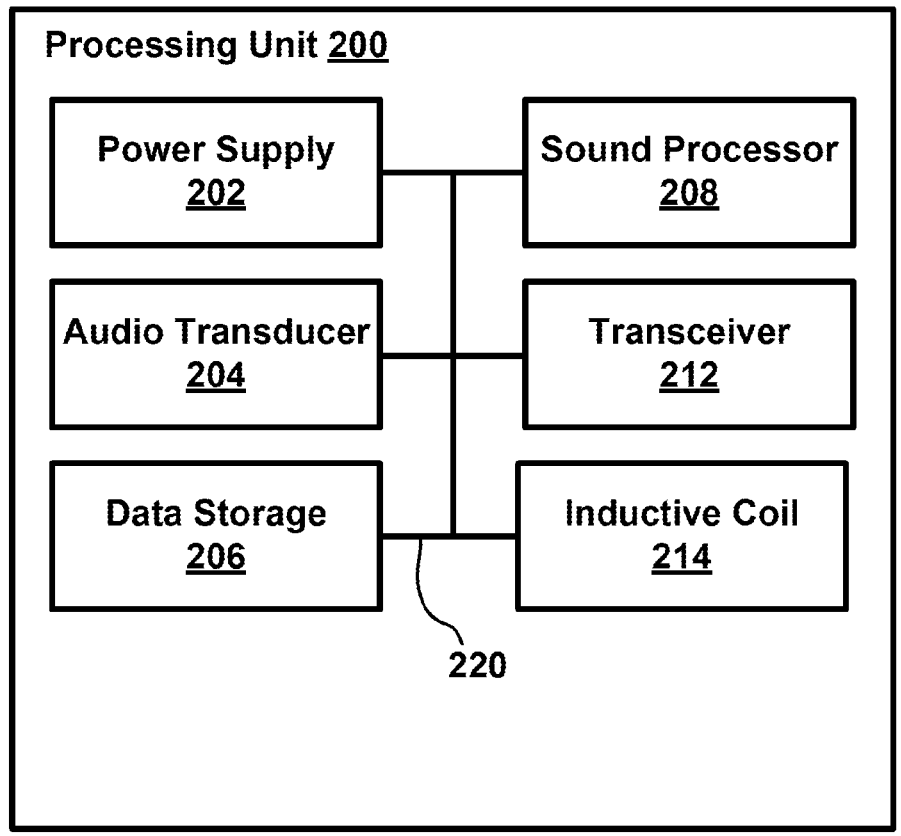
FIG. 2 is a block diagram of a processing unit depicted in FIG. 1A, according to an example.

FIG. 2 is a block diagram of a processing unit 200 of an auditory device. The processing unit 200 is one example of the processing unit 110 depicted in FIG. 1A. The processing unit 200 includes a power supply 202, an audio transducer 204, a data storage 206, a sound processor 208, a transceiver 212, and an inductive coil 214, all of which may be connected directly or indirectly via circuitry 220.

The power supply 202 supplies power to various components of the processing unit 200 and can be any suitable power supply, such as a rechargeable or non-rechargeable battery. In one example, the power supply 202 is a non-rechargeable battery that can be easily replaced when it becomes depleted. In another example, the power supply 202 is a rechargeable battery and can be disconnected from the processor, recharged, and re-connected at a later date. In another example, the power supply 202 is a non-replaceable rechargeable battery that is recharged wirelessly such as through an inductive power transfer system. The power supply 202 also provides power to the implanted unit of the auditory device 100 via the inductive coil 214.

The audio transducer 204 receives a sound from an environment and sends a sound signal to the sound processor 208. In one example, the processing unit 200 is part of a bone conduction device, and the audio transducer 204 is an omnidirectional microphone. In another example, the processing unit 200 is part of a cochlear implant, an auditory brain stem implant, a direct acoustic stimulation device, a middle ear implant, or any other auditory device now known or later developed that is suitable for assisting a user of the auditory device 100 in perceiving sound. In this second example, the audio transducer 204 is an omnidirectional microphone, a directional microphone, an electro-mechanical transducer, or any other audio transducer now known or later developed suitable for use in the type of auditory device employed. Furthermore, in other examples the audio transducer 204 includes one or more additional audio transducers.

The data storage 206 includes any type of non-transitory, tangible, computer readable media now known or later developed configurable to store program code for execution by a component of the processing unit 200 and/or other data associated with the processing unit 200. The data storage 206 also stores information indicative of a dynamic range for the electrodes L1-L8 of the electrode array 114. The data storage 206 may also store software programs executable by the sound processor 208.

The sound processor 208 receives an audio signal and processes the audio signal to determine a stimulation signal suitable for use by the auditory device, such as in an implanted unit associated with the auditory device. In one example, the sound processor 208 is a digital signal processor. In another example, the sound processor 208 is any processor or microcontroller or combination of processors and microcontrollers now known or later developed suitable for use in an auditory device. Additionally, the sound processor 208 may include additional hardware for processing the audio signal, such as an analog-to-digital converter and/or one or more filters.

The sound processor 208 is configured to receive the audio signal from the audio transducer 204 in the form of the sound signal. In processing the audio signal, the sound processor 208 identifies an SPL of the audio signal at one or more frequencies. The sound processor 208 accesses the data storage 206 to identify information indicative of the dynamic range for one or more of the electrodes L1-L8 in order to generate the stimulation signal. Based on the SPL of the sound at a given frequency, the sound processor 208 determines which of the electrodes L1-L8 need to stimulate the user's cochlea to allow the user to perceive the sound. The sound processor 208 determines the current to be applied through one or more of the electrodes L1-L8 to stimulate the user's cochlea based on the electrodes' dynamic range, also known as maps.

The transceiver 212 receives the stimulation signal from the sound processor 208 and modulates the stimulation signal to form a transmission signal. The transmission signal also includes the power signal received from the power supply 202. In one example, the transceiver 212 modulates the stimulation signal using a time-division multiple-access modulation scheme. In another example, the transceiver 212 uses any modulation scheme now known or later developed suitable for inductively transmitting the stimulation signal to an implanted unit of an auditory device. The transceiver 212 sends the transmission signal to the inductive coil 214.

The inductive coil 214 receives the transmission signal from the transceiver 212 and inductively transmits the transmission signal to the implanted unit 112. The inductive coil 214 is constructed of any material or combination of materials suitable for inductively transferring a power signal to the implanted unit.

Figure 3:
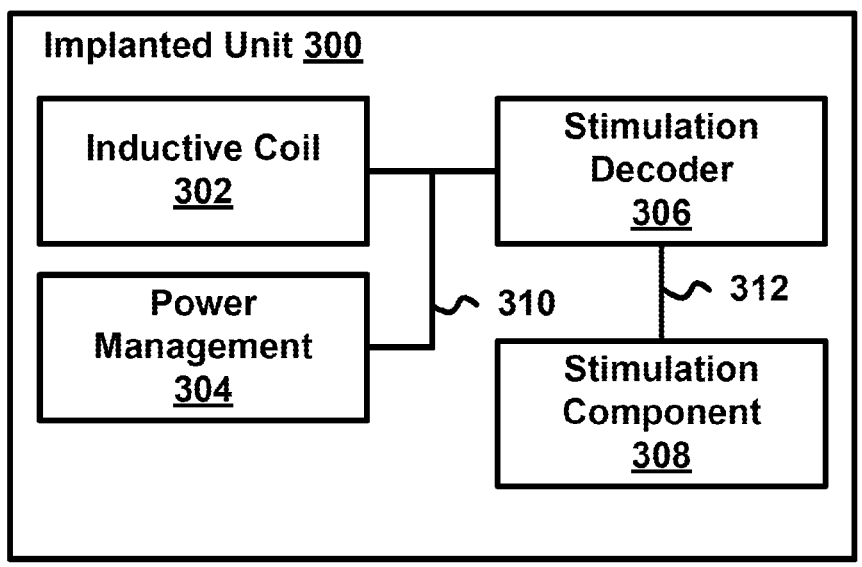
FIG. 3 is a block diagram of an implanted unit depicted in FIG. 1A, according to an example.

FIG. 3 is a block diagram of an implanted unit 300 of an auditory device, such as a cochlear implant. The implanted unit 300 is one example of the implanted unit 112 depicted in FIG. 1A. The implanted unit 300 includes an inductive coil 302, power management 304, and a stimulation decoder 306, all of which are connected directly or indirectly via circuitry 310. The implanted unit 300 also includes a stimulation component 308 that is connected to the stimulation decoder 306 via circuitry 312. The stimulation component 308 is an example of a stimulation device.

The inductive coil 302 receives the transmission signal from the processing unit 110. The inductive coil 302 is constructed of any biocompatible material or combination of materials suitable for inductively receiving power from the processing unit 200. The inductive coil 302 transfers the power signal to the power management 304. Alternatively, the implanted unit 300 may not include the power management 304. In this case, the inductive coil 302 transfers the power signal to the stimulation decoder 306 and the stimulation component 308.

The power management 304 receives the transmission signal from the inductive coil 302 and distributes power to the components of the implanted unit 300. The power management 304 also includes a component suitable for removing the coded stimulation signal from the power signal. The power management 304 sends the coded stimulation signal to the stimulation decoder 306. The stimulation decoder 306 decodes the coded stimulation signal and transfers the stimulation signal to the stimulation component 308.

The stimulation component 308 receives the stimulation signal from the stimulation decoder 306 and generates a stimulus based on the stimulation signal. In one example, the stimulation component 308 includes a first subcomponent configured to generate the stimulus and a second subcomponent configured to deliver the stimulus to an auditory organ, such as a cochlea, an auditory nerve, a brain, or any other organ or body part capable of assisting a user of the auditory device in perceiving at least a portion of a sound. The first subcomponent generates the stimulus based on the stimulation signal and sends the stimulus to the second component. The second subcomponent delivers the stimulus to the body part of the user.

For instance, since implanted unit 300 is part of a cochlear implant in the illustrated example, the stimulation component 308 includes a signal generator and the electrode array 114. The signal generator generates an electrical signal based on the stimulation signal and sends the electrical signal to the electrode array 114. The electrical signal causes one or more of the electrodes L1-L8 to deliver one or more electrical stimuli to a portion of the user's cochlea. The one or more electrical stimuli cause the cochlea to stimulate the user's auditory nerve, thereby allowing the user to perceive at least a portion of a sound.

In another example, the stimulation component 308 stimulates a different body part of the user. For instance, if the auditory device is an auditory brain stem implant, the stimulation component 308 provides the stimulation signal directly to the user's brain. In this case, the stimulation component 308 includes an electrode array that is implanted in the user's brain. The electrical signal is sent to the electrode array 114, causing one or more electrodes located on the array to deliver an electrical stimulus to a portion of the user's brain. The stimulus causes the user to perceive at least a characteristic of the sound.

Figure 4:
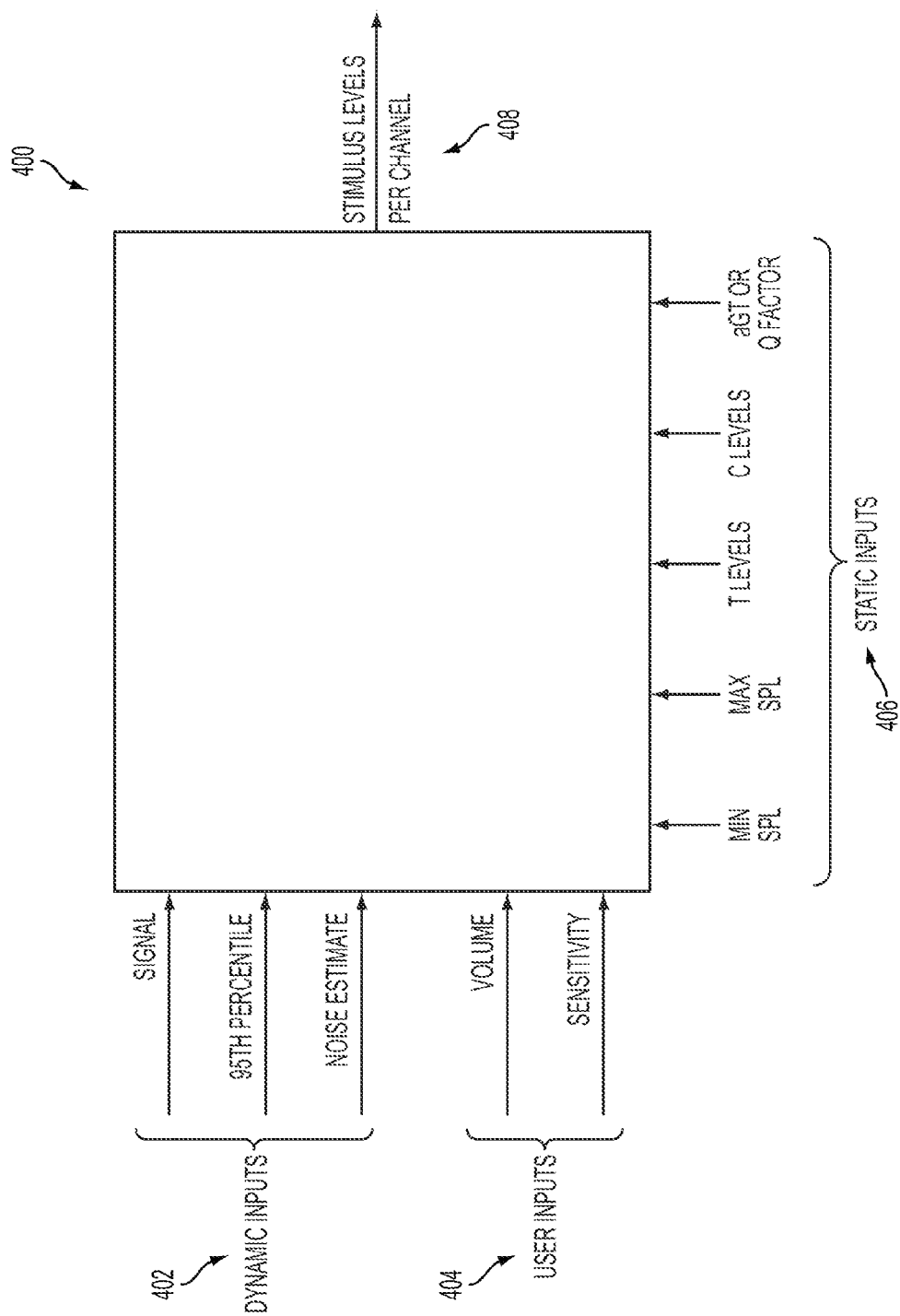
FIG. 4 is a functional block diagram illustrating a model of inputs and outputs that may be included in various embodiments.

FIG. 4 is a functional block diagram illustrating a model 400 of inputs and outputs that may be utilized by a processor, such as the sound processor 208, to determine the dynamic range, according to various embodiments. The model 400 includes a plurality of dynamic inputs 402, a plurality of user inputs 404, a plurality of static inputs 406, and an output 408.

The model 400 is preferably implemented as a set of computer-readable instructions stored on a computer-readable medium configured to cause a processor to perform functions described by the instructions. For example, the instructions may be software or firmware stored on a memory, such as in the data storage 206. Alternatively, the model 400 may be implemented partly or entirely by hardware, such as one or more electronics components. The model 400 preferably receives and stores inputs in a memory, such as the data storage 206, accessible by the processor. A user interface may be included to allow a user or device to provide one or more of the inputs to the model 400. The output preferably consists of one or more signals and/or stored data values to be used to provide stimulation. According to one example, the processor is the sound processor 208, the computer-readable medium is the data storage 206, and the output is the transceiver 212 and inductive coil 214.

The plurality of dynamic inputs 402 includes a signal input, a measure input, and a noise estimate input. Each of these dynamic inputs 402 is updated periodically, predictably, or sporadically. For example, one or more of the dynamic inputs 402 could be updated for each sample of the input audio signal received at the auditory device. The signal input is preferably a channelized version of the input audio signal. The measure input is preferably a statistical measure of upper bounds of the input audio signal, such as a percentile estimate, determined by a processing unit, such as the sound processor 208. For example, the measure input could be a $95^{th}$-percentile estimate of the channelized input audio signal. The noise estimate input is preferably performed with a process, such as within a preliminary noise reduction process. While the plurality of dynamic inputs 402 preferably comprises the above-described three inputs, more or fewer dynamic inputs may also be included in some embodiments.

The plurality of user inputs 404 includes a volume input and a sensitivity input. Each of these user inputs 404 is updated on an asynchronous basis, but while the model is operating. The user inputs 404 are variable parameters that the user can adjust to change listening quality. For example, the volume input adjusts a maximum volume to be assigned to a maximum (or near-maximum) stimulation experienced by the user (i.e. an upper value of an input dynamic range). The sensitivity input adjusts a minimum volume to be assigned to a minimum (or near-minimum) stimulation experienced by the user (i.e. a lower value of the input dynamic range). While the plurality of user inputs 404 preferably comprises the volume and sensitivity inputs, more or fewer user inputs may also be included in some embodiments. In some embodiments, there are no user inputs 404.

The plurality of static inputs 406 is a set of fixed parameters that remain unchanged while the model is operating and should be set before operation of the auditory device. For example, one or more of the static inputs are user-specific (e.g. recipient-specific) parameters set by an audiologist during fitting of the auditory device. As another example, one or more of the static inputs 406 are device-specific parameters related to the particular auditory device (e.g. make, model, and/or unique device).

The plurality of static inputs 406 includes a minimum sound pressure level (Min SPL) input, a maximum sound pressure level (Max SPL) input, a T-Level input, a C-Level input, and Q-Value input (also called a Q-Factor input herein). The Min SPL input is a device-specific parameter corresponding to the functional noise floor of the stimulation device. The Max SPL input is a device-specific parameter corresponding to a maximum value of an analog-to-digital converter in the stimulation device. The T-Level input is a user-specific parameter (e.g. set by an audiologist) that serves as a minimum (or near minimum) of an electrical dynamic range of the acoustic-to-electric mapping function. The C-Level input is a user-specific parameter (e.g. set by an audiologist) that serves as a maximum (or near maximum) of an electrical dynamic range of the acoustic-to-electric mapping function. The Q-Value input is an input corresponding to the shape of the mapping function. The Q-Value should be fixed for even loudness spacing between current steps (if electrical stimulation is used) or should be adjusted to produce an appropriate curve for a natural-sounding output signal for acoustic applications, such as hearing aid devices.

The output 408 of the model 400 is a functional representation of a stimulus level to be applied to the user by a stimulation device associated with the auditory device. Thus, a mapping according to the model 400 includes determining a stimulus level according to one or more of a stimulus level, current level, a pulse width, a vibration rate, and an interphase gap. For example, for electrical stimulation, the output 408 may include information for use in determining a signal amplitude, a pulse width, or an interface gap for the stimulation signal, or some combination of these, for example. For acoustic or vibratory stimulation, the output 408 may represent a speaker's output volume or amplitude or vibratory output amplitude or volume, for example.

Figure 5:
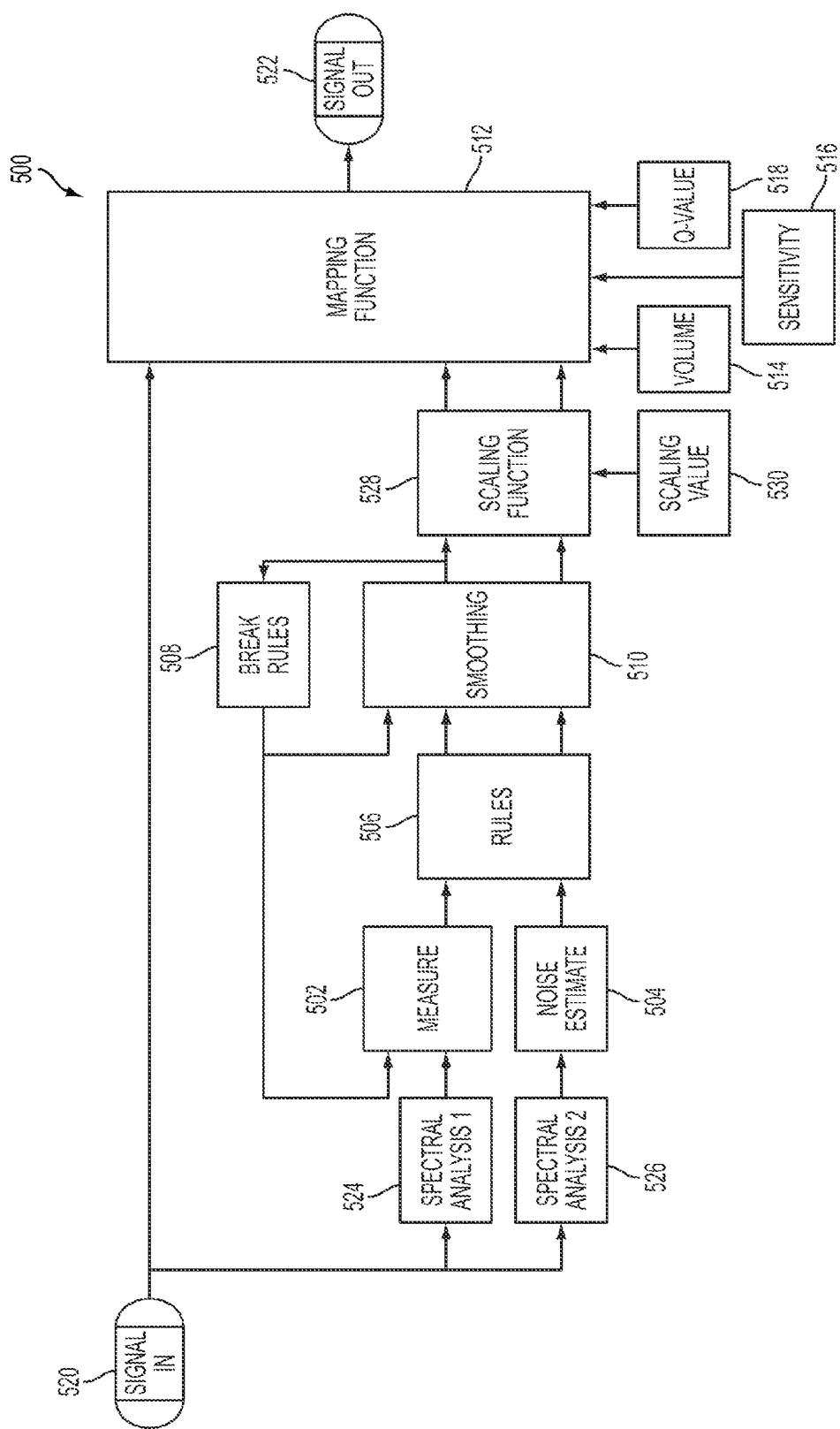
FIG. 5 is a functional block diagram illustrating a device for dynamically adjusting an input dynamic range and mapping the input signal to a new output signal, in accordance with embodiments of the present invention.

FIG. 5 is a functional block diagram illustrating a device 500 for dynamically adjusting an input dynamic range, in accordance with embodiments of the present invention. Such a device could be used in place of typical, more complex, multi-stage solutions, with possibly only front-end beam forming and weak front-end noise reduction remaining from such solutions, for example. The device 500 includes a measure module 502, a noise estimate module 504, a rules module 506, a break rules module 508, a smoothing module 510, a scaling function module 528 having a scaling value input 530, and a mapping function module 512 having as inputs a volume input 514, a sensitivity input 516, and a Q-Value input 518. The device 500 performs operations on an input signal 520 to obtain an output signal 522. A flow-forward structure is illustrated for slow SPL adjustments, while a feedback structure is illustrated for fast CSPL changes (e.g. see the description accompanying the break rules module 508, below). The device 500 can be utilized on a per-channel or multi-channel (clustered) basis, as well as on FFT bins (e.g. for acoustic applications) or in a broadband implementation. In preferred embodiments, for example, the device 500 could operate using 22 channels (electric) or 65 bins (acoustic).

The measure module 502 preferably takes in the input signal 520 (or, alternatively and as illustrated in FIG. 5, a multi-channel signal via spectral analysis 2 module 524) and a break signal from the break rules module 508 to determine (1) an amplitude data (e.g. a percentile estimate or other measure), (2) a time constant for the measure, and (3) an initial condition. If the measure is a percentile estimate, then the measure module 502 calculates a percentile estimate (e.g. 95%), in which the smoothed output will have 95% of the input signal amplitude below it and 5% of the input signal amplitude above it. In essence, the measure module 502 is tracking the peaks in the signal when it calculates a percentile estimate. The percentile estimate may range from 70-100%, for example. In another example, the percentile estimate may be 50%, which may be more advantageous for certain acoustic auditory devices. In some embodiments, several measure modules may be included in parallel with one another, each calculating a different selectable percentile estimate (e.g. 70%, 75%, 80%) that may be used to define a dynamic-range mapping curve. In other embodiments, one or more measure modules may calculate a different percentile estimate for each spectral channel. As described below with respect to the break rules module 508, under some circumstances, the break signal is activated, which quickly changes the mapping curve according to a pertinent break rule from the break rules module 508. The output of the measure module 502 is preferably used to set a dynamic CSPL to be used for mapping the input audio signal to a corresponding output stimulation.

The noise estimate module 504 preferably takes in the input signal 520 (or a multichannel signal 526) and provides a mean noise level estimate as its output. Any of a variety of suitable known noise estimation strategies, such as those currently used in certain hearing prostheses, may be utilized to determine this mean noise level. One example would be to use a percentile estimate such as the 25th percentile estimate. Other examples of concepts relating to noise estimation strategies may be found in the following two articles, the contents of both of which are incorporated by reference herein: R. Martin, "Noise Power Spectral Density Estimation Based on Optimal Smoothing and Minimum Statistics," *IEEE Trans. On Speech and Audio Processing*, vol. 9, no. 5, pp. 504-512, July 2005, and I. Cohen, "Noise Spectrum Estimation in Adverse Environments: Improved Minima Controlled Recursive Averaging," *IEEE Trans. On Speech and Audio Processing*, vol. 11, no. 5, pp. 466-475, September 2003. The noise estimate module 504 preferably uses an adaptation time of around 1 second. The output of the noise estimate module 504 is preferably used to set a dynamic TSPL to be used for mapping the input audio signal to a corresponding stimulation.

As noted above, both the measure module 502 and the noise estimate module 504 receive an input signal, which may be the whole input signal 520, or multiple spectrally limited signals such as FFT bins or channels (via spectral analysis 1 module 524 and spectral analysis 2 module 526, respectively). In some embodiments, the number of spectral bands, and/or the widths of spectral bands used for the measure and for the noise estimate may not be the same. In such a case, the input signal measure with the greatest number of spectral bins preferably should determine the number of spectrally limited mapping functions. For instance, the measure may be calculated on a broadband signal provided by spectral analysis 1 module 524, while the noise estimate may be calculated for 22 spectral channels provided by spectral analysis module 526. In this case, the measure would be used for each of the 22 spectral channel mapping functions. Where partially overlapping spectral bands exist between measures, an average, weighted average, minimum, or maximum value may be used for each measure to determine the measure or noise estimate for each mapping function.

The rules module 506 helps to ensure that the outputs of the measure module 502 and/or the noise estimate module 504 result in a viable input dynamic range. In other words, the rules module 506 constrains the absolute and relative inputs used for mapping in order to prevent the auditory device from entering extraneous states.

Figure 6:
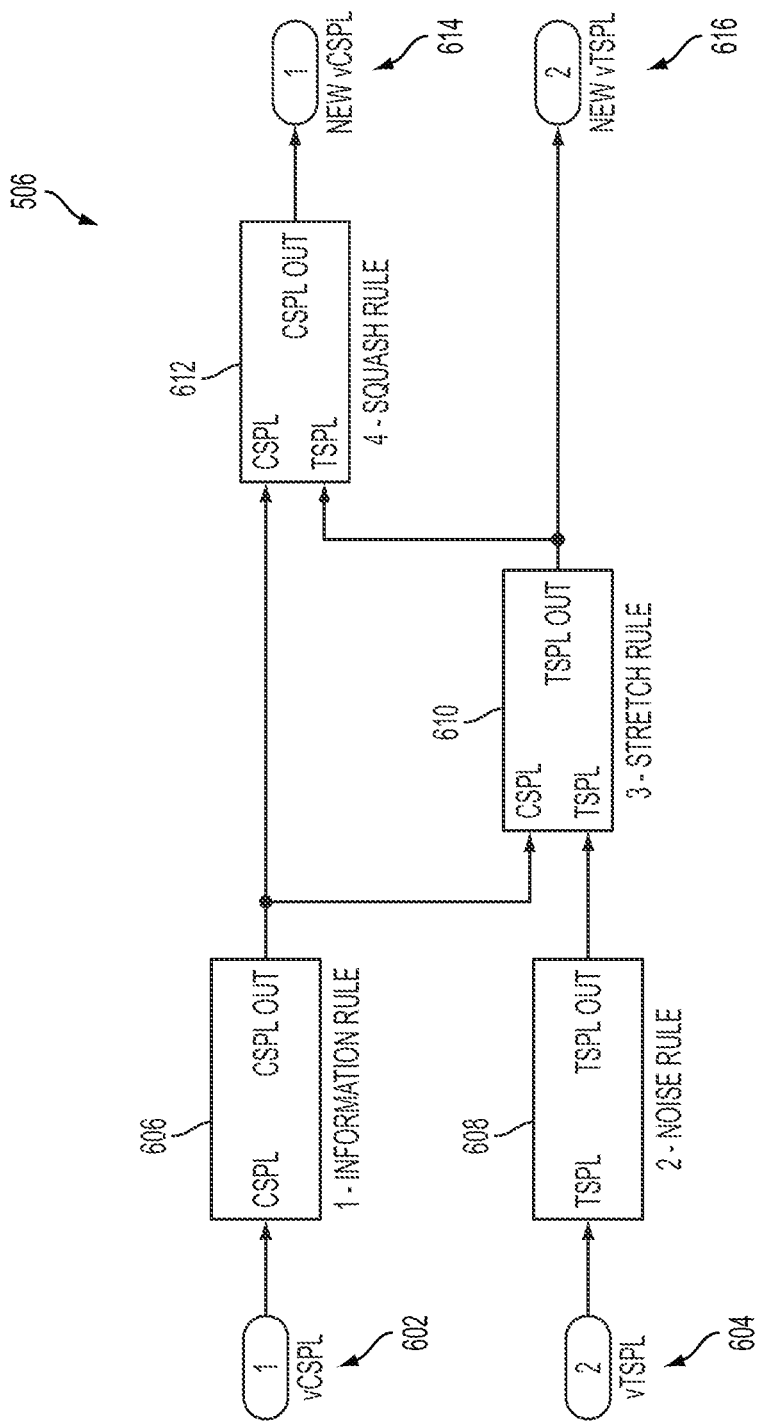
FIG. 6 is a functional block diagram illustrating the rules module of the device of FIG. 5, according to an example.

FIG. 6 is a functional block diagram illustrating the rules module 506 in further detail, according to an example. As shown, two inputs to the rules module 506 are a dynamic CSPL input 602 and a dynamic TSPL input 604, which are the outputs from the measure module 502 and the noise estimate module 504, respectively.

A first rule imposed by the rules module 506 is an information rule applied by an information rule module 606. The information rule essentially limits the absolute values of the dynamic CSPL, by preventing the dynamic CSPL from going above a maximum limit, which may be approximately 90 dB, for example. This 90 dB limit is slightly below a maximum limit for a typical analog-to-digital converter (given a specific microphone and amplifier combination). In addition, the information rule limits the absolute values of the dynamic CSPL from going below a minimum limit, which may be approximately 40 dB, for example. One example circumstance in which the information rule is likely to be invoked is when there is silence. In such a case, the dynamic TSPL input 604 would tend toward the noise floor of the input microphone and the dynamic CSPL input 602 would also decrease toward the same value. However, by applying the information rule, the dynamic CSPL is constrained to the minimum limit.

A second rule imposed by the rules module 506 is a noise rule applied by a noise rule module 608. The noise rule is similar to the information rule, and essentially prevents the noise estimate (dynamic TSPL) from going as low as the noise floor of the input microphone plus a buffer to account for system noise, which may be 20 dB, for example. It also prevents the dynamic TSPL from going too high (e.g. more than around 60 dB).

A third rule imposed by the rules module 506 is a stretch rule applied by a stretch rule module 610. The stretch rule prevents the input dynamic range from being too large, preferably by increasing the dynamic TSPL level to ensure that the input dynamic range does not exceed a maximum value, such as 50 dB. For example, in a listening environment having loud speech with negligible environmental noise, the noise floor (dynamic TSPL) will be small and the dynamic CSPL will be large. By increasing the dynamic TSPL (i.e. maintaining the dynamic CSPL, in accordance with the first rule, above), the stretch rule helps to ensure that system noise and low level environmental noise are mapped out of the stimulation.

A fourth rule imposed by the rules module 506 is a squash rule applied by a squash rule module 612. The squash rule prevents the input dynamic range from being too small, preferably by increasing the dynamic CSPL to ensure that the input dynamic range is larger than a minimum value, such as 30 dB. For example, in a listening environment having constant environment noise, the noise estimate (dynamic TSPL) and dynamic CSPL will tend to become quite similar. By increasing the dynamic CPSL (i.e. maintaining the dynamic TSPL, in accordance with the second rule, above), the squash rule helps to ensure that the noise is mapped to a lower stimulation level.

While the rules module 506 preferably applies all four of the above rules, in some embodiments, fewer or more rules may be applied. The rules are preferably applied in a cascade order so that the desired outcome is not undone by one or more previous rules. A preferred outcome of the application of the above rules is that the minimum dynamic TSPL will be approximately 25 dB, the maximum dynamic CSPL will be approximately 90 dB, and the dynamic range will be between approximately 30 dB and approximately 50 dB. The outputs of the rules module 506 are a new dynamic CSPL output 614 and a new dynamic TSPL output 616 that can be subsequently smoothed and mapped.

In a preferred implementation, the upper value maximum limit is approximately 90 dB, the upper value minimum limit is approximately 40 dB, the lower value maximum limit is approximately 60 dB, the lower value minimum limit corresponds to a noise floor of a microphone associated with the auditory device, the maximum difference threshold is approximately 50 dB, and the minimum difference threshold is approximately 30 dB.

The break rules module 508 receives the audio input signal 520 and the current CSPL level (from the smoothing module 510) as inputs and, if necessary, applies relatively fast changes to the CSPL. While the measure module 502, noise estimate module 504, and smoothing module 510 make relatively slow changes to the CSPL and/or TSPL, in order to improve listening quality, the break rules module 508 overrides these other modules when a fast gain change needs to be made. For example, if the audio input signal 520 (or a function of the audio input signal) exceeds the current dynamic CSPL level by a certain threshold amount, then the break rules module 508 causes the dynamic CSPL to be increased on a fast time constant basis, overriding the slow time constants of the system.

There are at least four ways in which the break rules module 508 can respond to an input audio signal that exceeds the current CSPL level by the certain threshold amount. A first way would be to do nothing, which causes at least a portion of the input audio signal to be above the output CSPL, potentially making it uncomfortably loud, until the slower time constants has changed the dynamic CSPL, lowering the output signal. A second way would be to quickly and temporarily increase the dynamic CSPL to a suitably high level, and then decrease it back to the dynamic CSPL (either quickly or slowly) after the exceeding input audio signal is no longer present. A third way would be to quickly increase the dynamic CSPL to a suitably high level by changing the measure and the smoothing of the measure, which may also require increasing the dynamic TSPL to maintain a suitably-sized input dynamic range. Finally, a fourth way would be to increase the dynamic CSPL to an intermediate level (e.g. halfway) between the original dynamic CSPL and the level related to the new input audio signal. Each of these has its advantages and disadvantages, and the selection of a particular technique can be user- or audiologist-selectable, or it can be set in the device during manufacture or provisioning, for example.

The smoothing module 510 smooths changes in the dynamic CSPL and dynamic TSPL to mitigate abrupt mapping changes and in order to provide the user with the ability to better hear relative loudness, while maintaining performance. Where there are multiple spectral channels and therefore multiple mapping functions, the smoothing time may also vary across spectral channels.

One way to do this is for the smoothing module 510 to introduce a relatively long time constant (e.g. 30 seconds for dynamic CSPL) to changes in the dynamic CSPL and dynamic TSPL. Time constants may range from 2-180 seconds, for example, to provide suitable adaptation times. In contrast, the time constants used in the measure module 502 and noise estimate module 504 are preferably much shorter (on the order of 1 second) and attempt to provide the best estimates possible. The smoothing module 510 has as its inputs a break input from the break rules module 508 and the new dynamic CSPL input and new dynamic TSPL input received from the rules module 506. As outputs, the smoothing module 510 outputs a smoothed dynamic CSPL output (provided as an input to the break rules module 508 and to the mapping function module 512) and a smoothed dynamic TSPL output provided to the mapping function module 512.

Thus, according to one example relating to dynamic CSPL, if an audio input signal becomes on-average louder, the signal will be above dynamic CSPL (e.g. in the CSPL+10% region) and will be perceived as loud for about 30 seconds (corresponding to the time constant of the smoothing module 510) before the smoothing module 510 causes the dynamic CSPL level to increase and make the loud signal comfortable again (i.e. at the C-Level). Conversely, if an audio input signal becomes on-average softer, the signal will be below dynamic CSPL and be perceived as soft for about 30 seconds before the dynamic CSPL level decreases and makes the soft signal comfortably loud (more easily hearable) again.

Similarly, for dynamic TSPL, the smoothing module 510 attempts to change the noise floor more slowly (e.g. with a 5 second time constant) than the short time constant (e.g. 1 second) typically implicit in noise estimation. This will help to improve comfort and performance.

The smoothing module 510 may alternatively or additionally utilize a moving average to accomplish smoothing. For example, if the system 500 stores a history of past determined dynamic TSPL and dynamic CSPL levels in a memory associated with the auditory device (such as in the data storage 206), the smoothing module 510 can periodically calculate a moving average of those stored determined levels. In a further embodiment, in order to introduce a predictive aspect to the smoothing, an autoregressive moving average (ARMA) may be utilized by the smoothing module 510. In a further embodiment, a finite impulse response (FIR) or infinite impulse response (IIR) filter may be used, where the desired smoothing is achieved by adjusting the given time constants of the FIR or IIR filter. In still other embodiments, the mapping function 512 may also make use of a moving average, FIR, or IIR filter instead of or in addition to smoothing module 510. The use of a moving average, FIR, or IIR filter in smoothing may be particularly beneficial for acoustic-to-acoustic mappings.

In a preferred embodiment, adaptation times are controlled to provide desired performance outcomes. Slow adaptation of the noise floor (noise estimate) and the measure (e.g. percentile estimate) should be used to determine the dynamic TSPL and dynamic CSPL, and therefore, the dynamic range. Small deviations (e.g. less than 10 dB, for example) for short term periods should be possible, such as a fast time constant change (e.g. from the break rule), to increase the dynamic CSPL temporarily, in order to decrease the effect on longer-term dynamic CSPL levels from the user's own voice. Table A, below, illustrates presently preferred time constants. Other time constants, such as those determined during bench testing and/or normal hearing testing, may be more desirable for particular applications. Again, in general, relatively long (slow) adaptation times are used for the noise estimate (dynamic TSPL) and measure (dynamic CSPL), while a short (fast) adaptation time is used when a break rule applies.

TABLE A

| | Rise/Fall times | | | |
|---|---|---|---|---|
| | Short term rise | Short term fall | Long term rise | Long term fall |
| TSPL | NA | NA | 5 seconds | 20 seconds |
| CSPL | 0.01 seconds | 0.1 seconds | 20 seconds | 60 seconds |

The mapping function module 512 maps the important part of the signal (e.g. speech segments) using the electrical dynamic range. In a presently preferred embodiment, the mapping is a mostly linear mapping from SPL-to-current level (e.g. dynamic TSPL is mapped to an output T-Level and dynamic CSPL is mapped to C-Level). To allow for some overhead above the C-Level, dynamic CSPL may be mapped to a sub-maximal comfort level (e.g. C-Level minus 10%) or the C-Level could be correspondingly increased (e.g. C-Level+10%). In other embodiments, the mapping may map input SPL to output SPL (see FIG. 8).

The mapping function module 512 receives as inputs the input audio signal 520 to be mapped, the smoothed dynamic CSPL, and the smoothed dynamic TSPL. Additional inputs may include a volume input 514, a sensitivity input 516, and a Q-Value input 518. The volume input 514 and sensitivity input 516 are preferably set by the user to change a point on the mapping curve (see FIGS. 7 and 8) relative to the dynamic CSPL and/or dynamic TSPL, while the Q-Value input 518 is preferably set internally in the auditory device. An additional input that could also be included is a scaling value input 530 that mixes between the relative loudness described above, which has dynamic TSPL and dynamic CSPL values, and an absolute loudness that has a fixed TSPL and CSPL mapping (e.g. at 25 dB and 65 dB, respectively). Such a scaling value input 530 could be used to scale between relative (dynamic SPL values) and absolute (fixed SPL values) loudness to suit user preference (via scaling function module 528). The scaling function module 528 effectively scales between a fixed TSPL and a fixed CSPL (i.e. absolute loudness) and the dynamic TSPL and dynamic CSPL described above, in accordance with the value provided as the scaling value input 530. For example, a value of [0,0] at the scaling value input 530 could mean to operate with fixed CSPL and fixed TSPL (i.e. dynamic range altering is turned off); a value of [0,1] could mean to operate with a fixed CSPL and a dynamic TSPL; a value of [0.5,0] could mean to operate with the average of the fixed and dynamic CSPL and a fixed TSPL; and a value of [1,1] could mean to operate with a dynamic CSPL and a dynamic TSPL. The mapping function module 512 outputs an output signal 522 representative of the stimulus signal to be applied to the user. While the output is illustrated as being a current level value in acoustic-to-electrical applications in the example of FIG. 7, the output could alternatively be an SPL output, for example, for acoustic-to-acoustic applications.

Similar to as described above with respect to the smoothing module 510, the mapping function 512 may include smoothing functionality, where changes to the output signal 522 from the mapping function 512 are smoothed. For example, the mapping function 512 may include an FFT/iFFT algorithm having a large overlap (e.g. 87.5%) to provide smoothing, which may be beneficial for acoustic-to-acoustic applications. In such a case, a shorter input/output buffer may be utilized, if lower latency is desired.

In alternative embodiments, the mapping function module 512 uses to the two inputs from the scaling function module 528 (and other inputs, e.g., the input from volume module 514) to calculate a gain applied to the input audio signal 520 to generate the output signal 522.

The break rule 508 and adjustments to the input dynamic TSPL and input dynamic CSPL could each operate independent of the operation of the other two. For example, a fixed-input TSPL of 25 dB could be used with the break rules module 508 turned off (or omitted), but changes to the input dynamic CSPL could still be made in accordance with the embodiments described herein. As another example, an input dynamic TSPL could be used with the break rules module 508 turned on (or included), while keeping a fixed input CSPL, such as at 65 dB. Additional inputs could be specified to turn the break rules module 508 on or off. In general, it should be understood that each of the three above-mentioned components, input TSPL, input dynamic CSPL, and break rules module 508 is capable of operating independently of the other two components in some embodiments.

Figure 7:
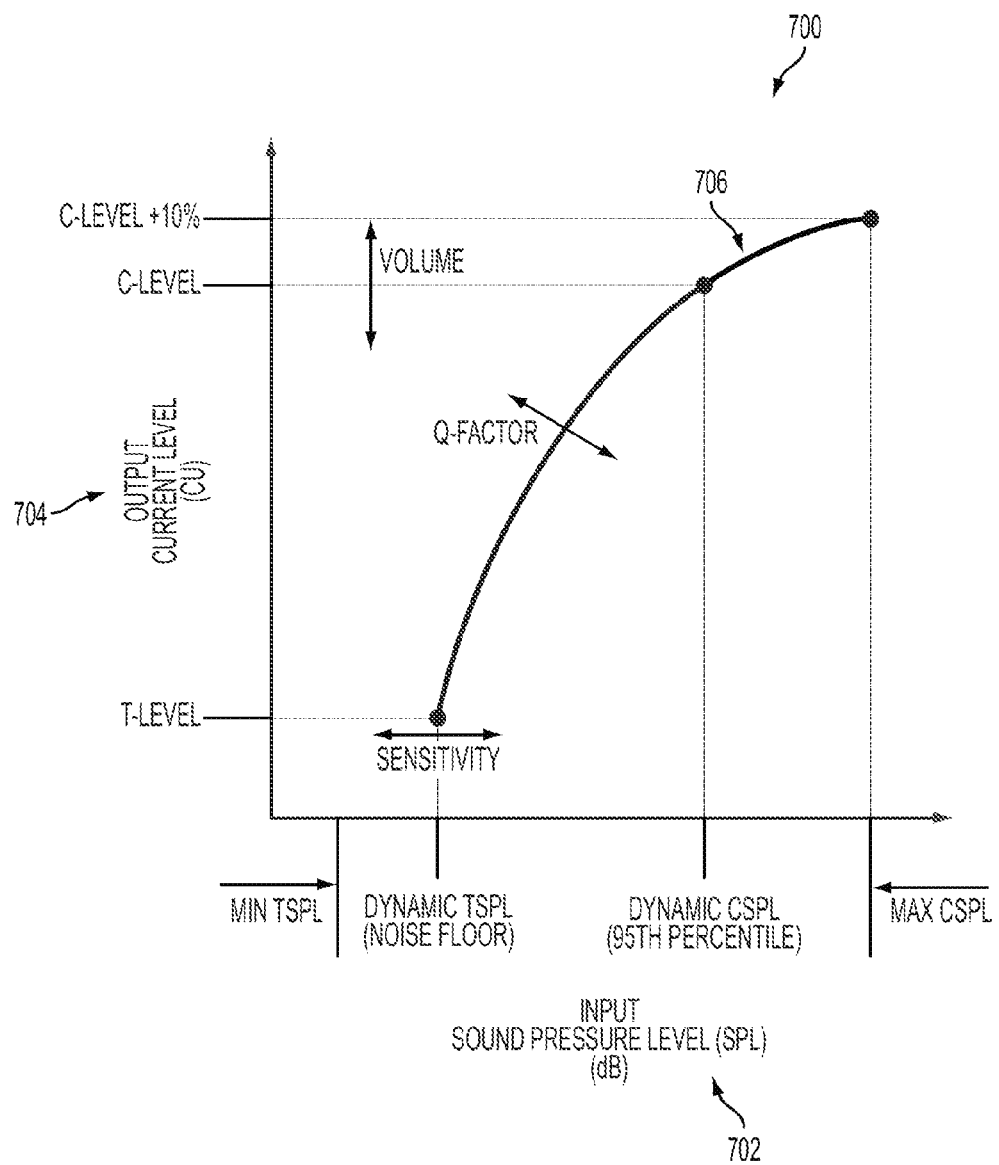
FIG. 7 is a graphical representation of an acoustic-to-electric mapping curve, according to an example.

FIG. 7 is a graphical representation 700 of an acoustic-to-electric mapping curve 706 embodying concepts described herein. The mapping curve 706 includes an acoustic x-axis 702 showing Sound Pressure Level (SPL) in dB and a corresponding electric y-axis 704 showing current level in Current Units (CU), where the units of current will vary depending on the particular application or the electrode used (e.g. cochlear implant, brainstem implant, midbrain implant, etc.). If the particular auditory device provides stimulation to more than one channel (e.g. where each channel stimulates at a different frequency range) or bin, then a separate mapping curve is preferably assigned to each such channel or bin.

As illustrated, the mapping curve 706 is a generally smooth curve having (1) a first approximately linear section (having a slope $a1x+b1$) at lower SPL, (2) a second approximately linear section (having a slope $a2x+b2$, where $a1>a2$ and $b1<b2$) at lower SPL, and (3) a shoulder region between the first and second approximately linear sections (near the 95th percentile SPL in the example shown). The general shape of the mapping curve 706 is typically chosen to approximate normal hearing or to accomplish a particular auditory goal associated with an auditory device's application. The Q-Factor (see the description accompanying the mapping function module 512 with reference to FIG. 5, above) can be pre-programmed, set by the user (e.g. using the Q-Value input 518), or calculated to satisfy a particular auditory goal. Varying the Q-Factor changes the shape (e.g. slope) of the mapping curve 706; for example, from a more-bowed curve to a flatter curve, or vice versa.

For acoustic applications, a curve that is less linear or even non-linear (e.g. exponential) might provide better performance. Adjustments to the Q-Factor will also likely be more applicable to an acoustic application, where changes to the shape of the mapping curve 706 could be relatively more significant compared to electrical stimulation applications.

Figure 9:
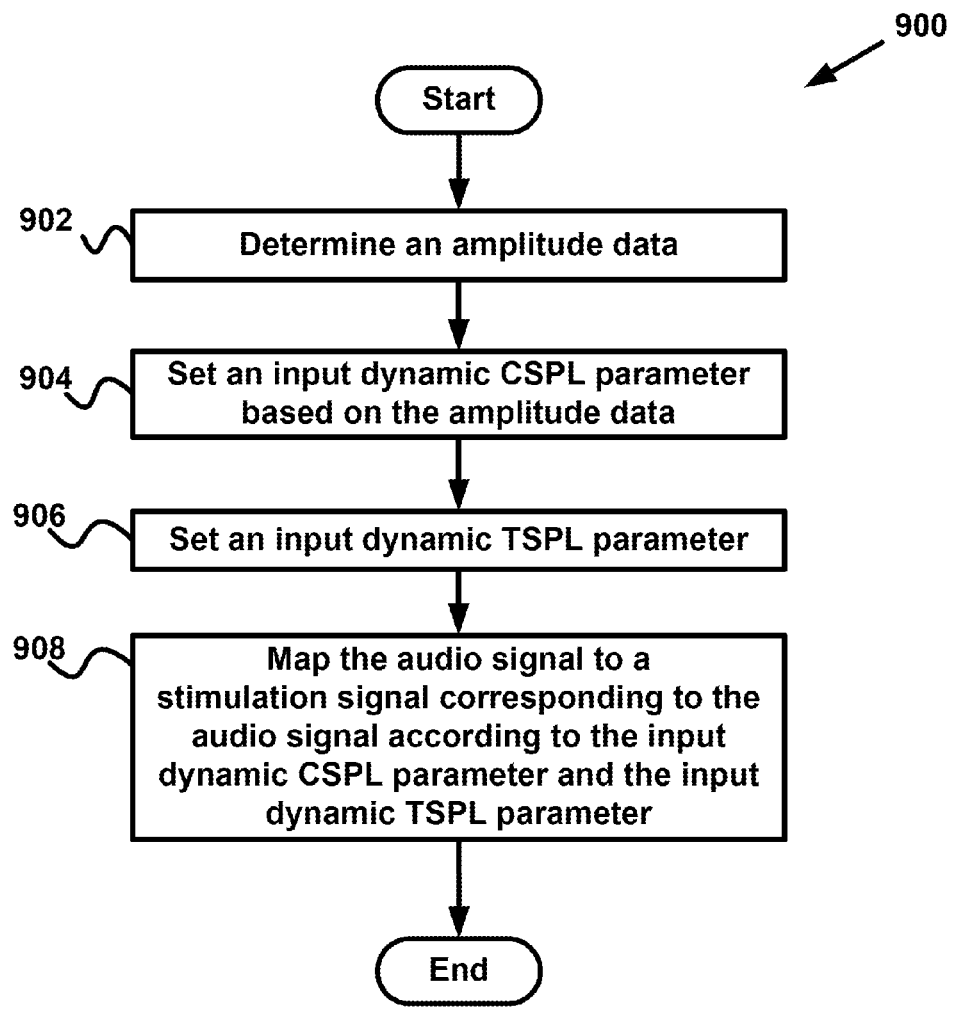
FIG. 9 is a flow diagram illustrating a method according to a first method.

In accordance with embodiments of the present invention, and as illustrated in the method 900 of FIG. 9 for processing an audio signal, such as an input audio signal, the mapping curve 706 is set as follows. The method 900 includes determining an amplitude data, such as a percentile estimate, representing a characteristic of an amplitude of the audio signal (block 902). According to one example, determining the amplitude data includes the measure module 502 determining a measure of a characteristic of an average peak amplitude of the audio signal, such as a percentile estimate.

The method 900 further includes setting an input dynamic CSPL parameter based on the determined amplitude measure (block 904). Using the example of FIG. 7, the input dynamic CSPL (representing an estimate of the signal's 95th percentile) is on the x-axis 702 and is set to map to the "C-Level" on the y-axis 704).

The method 900 further includes setting an input dynamic TSPL parameter (representing an estimate of the noise floor) (block 906). Referring to FIG. 7, the input dynamic TSPL parameter shown on the x-axis 702 is mapped to the T-Level on the y-axis 704. In one example, setting the input dynamic TSPL parameter includes determining a noise-level estimate during a noise smoothing time period and setting the input dynamic TSPL parameter to the noise-level estimate, as described above with respect to the smoothing module 510 of FIG. 5.

The points corresponding to the C-Level and T-Level, along with the Q-Factor, help to define the mapping curve 706, according to some embodiments. Also, as described above with reference to FIG. 5, the measure module 502, break rules module 508, and smoothing module 510 may be applied to the input dynamic CSPL and the dynamic TSPL. For example, in some embodiments, the break rules module 508 applies one or more of the first through fourth break rules (or a different break rule) in setting the input dynamic CSPL parameter and/or input dynamic TSPL parameter, as described with reference to FIG. 6.

Once the input dynamic CSPL parameter and the input dynamic TSLP parameter are set, resulting in a corresponding adjustment to or setting of the mapping curve 706, the method 900 includes mapping the audio signal to a stimulation signal corresponding to the audio signal according to the input dynamic CSPL parameter and the input dynamic TSPL parameter (block 908). This mapping is preferably constantly recalculated during operation of the system 500 by constantly determining new amplitude data (e.g. percentile estimates) and noise estimates. The method 900 may further include providing a stimulation, such as an electrical or acoustic stimulation, according to the stimulation signal. For example, in one embodiment, the stimulation signal is characterized by a predetermined C-Level current level and a predetermined T-Level current level, in which the input dynamic CSPL parameter is mapped to the C-Level current level and the input dynamic TSPL parameter is mapped to the T-Level current level.

Figure 8:
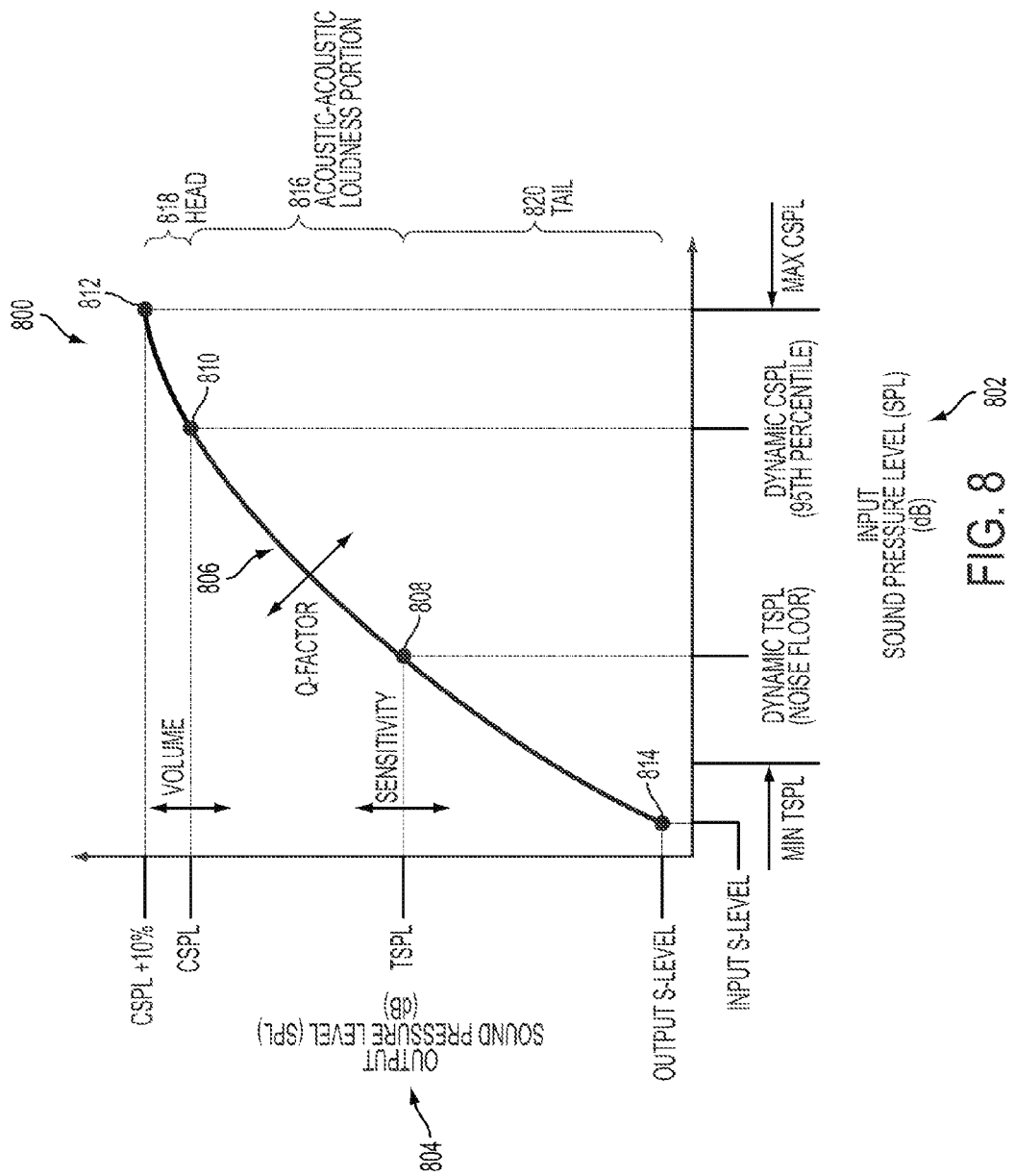
FIG. 8 is a graphical representation of an acoustic-to-acoustic mapping curve illustrating effects of adjustments to additional user inputs for the mapping function module, according to an example.

FIG. 8 is a graphical representation 800 of an acoustic-to-acoustic mapping curve 806 illustrating effects of adjustments to the additional user inputs for the mapping function module 512 described above with reference to FIG. 5. The acoustic-to-acoustic mapping curve 806 is similar to the acoustic-to-electric mapping curve 706, and a description of common elements between the two is not repeated here.

The mapping curve 806 includes a first point 808 corresponding to a dynamic TSPL, a second point 810 corresponding to a dynamic CSPL, a third point 812 corresponding to a maximum CSPL, and a fourth point 814 corresponding to an acoustic S-level.

The first point 808 represents an input dynamic TSPL parameter "TSPL" (Threshold Sound Pressure Level) that maps to a corresponding output SPL level (shown as output TSPL in FIG. 8). For example, according to one embodiment, the input dynamic TSPL parameter is set by determining a noise estimate, such as a mean-noise-level estimate, over a noise smoothing time period (e.g. 1 second) and setting the input dynamic TSPL parameter to that determined mean-noise-level estimate. The set dynamic TSPL parameter is mapped to the output TSPL level, which is preferably predetermined to match characteristics of the auditory device (e.g. a device-specific parameter) and the user (e.g. a user-specific (e.g. recipient-specific) parameter). For example, the output TSPL level may correspond to a point at which an associated stimulation at that output TSPL level allows the user to just barely perceive an indication of the audio signal.

The second point 810 represents an input dynamic CPSL parameter "CSPL" (Comfort Sound Pressure Level) that maps to a corresponding dynamic CSPL level (shown as "output CSPL" in FIG. 8). For example, according to one embodiment, the input CSPL parameter is set by determining a measure relating to an upper volume bounds, such as a percentile estimate representing a percentile of the signal amplitude of an input audio signal. The input dynamic CSPL parameter is set based on the determined measure. The set input dynamic CSPL parameter is mapped to the output CSPL level, which is preferably predetermined to match characteristics of the auditory device (e.g. a device-specific parameter) and the user (e.g. a user-specific (or recipient-specific) parameter). For example, the output CSPL level may correspond to a point at which an associated stimulation at levels above that output CSPL level becomes uncomfortable. The output TSPL and output CSPL serve as a respective minimum and comfortable level of an acoustic dynamic range of an acoustic-to-acoustic mapping function. Further modifications to the input dynamic TSPL and dynamic CSPL (e.g. due to application of rules and smoothing) may result in corresponding modifications to the dynamic range.

The third point 812 represents a maximum parameter "Max CSPL" that maps to a corresponding output level above the output CSPL level associated with the input dynamic CSPL parameter. In the example of FIG. 8, the input maximum CSPL is mapped to an output CSPL level that is the output CSPL+10%. While the output CSPL level is a "comfort" level, the level above the CSPL level will likely be uncomfortable (i.e. loud in volume) to the user, but not cause harm. However, since the output CSPL level can be set to a percentile estimate that is less than 100% of the input signal amplitude, the levels above the output CSPL level are not likely to be long in duration. To the extent they are, then the input dynamic CSPL parameter will be accordingly adjusted to reflect the new higher percentile estimate. Having an input dynamic range that allows for levels above and below the output CSPL level for a time period enables the user to better perceive differences in relative volume.

The fourth point 814 represents an S parameter "input acoustic S-Level" that maps to a corresponding output acoustic S-level. This fourth point 814 is preferably included to provide a map termination point for low sound pressure levels.

The first, second, third, and fourth points 808-814 lie on a curve and help to define the mapping curve 806, as each of these points lies on the mapping curve 806, according to a preferred embodiment. In addition, additional points on the mapping curve 806 may be introduced, such as one or more intermediate points between the first point 808 and the second point 810. For example, an additional percentile estimate might be introduced (e.g. at 75-percent) to better tailor the mapping curve 806 to a particular application and to provide a low gradient just below the dynamic CSPL parameter to present a significant portion of the loud acoustic signal near the output CSPL level. Fewer than the four points 808-814 may also be used, in some embodiments.

As shown in FIG. 8, the mapping curve 806 has three portions or segments: (1) an acoustic-acoustic loudness portion 816, (2) a head portion 818, and (3) a tail portion 820. The acoustic-acoustic loudness portion 816 includes the majority of the information in the input audio signal to be conveyed to the user. The head portion 818 is directed to higher-volume parts of the signal (i.e. those above the measure, such as those having a larger amplitude than a particular percentile estimate). The tail portion 820 is directed to sound pressure levels below the input dynamic TSPL parameter. As shown, the mapping curve 806 should be generally smooth (linear or near-linear, perhaps with a slight curvature to avoid any abrupt changes, such as near the CSPL, for example). Also as shown, acoustic-acoustic loudness portion 816 has an average slope greater than that of the head portion 818 and less than that of the tail portion 820. If additional points, beyond the first through fourth points 808-814 are included (such as intermediate points between the first and second points 808 and 810), then the mapping curve 806 may include more than three segments. The mapping curve 806 may alternatively comprise fewer than three segments.

FIG. 8 also illustrates how additional inputs, such as user inputs and static inputs, can affect the mapping curve 806, according to some embodiments. For example, the volume input 514 is preferably a user input that moves the second point 810 up or down in current level (or output SPL level), causing a corresponding perceived increase or decrease in volume at a particular current level (or SPL). In effect, the volume input 514 is thus adjusting the maximum of the electrical dynamic range (or output acoustic dynamic range). The sensitivity input 516 is preferably a user input that moves the first point 808 up or down in current level (or output acoustic dynamic range), causing a corresponding perceived increase or decrease in output current levels (or output SPL). The sensitivity input 516 is, therefore, used to adjust the minimum current level (or SPL). The Q-Value input 518 is preferably a static input set internally in the auditory device to adjust the acoustic-electric loudness portion 816. As shown in FIG. 8, adjusting the Q-Value input 518 causes the acoustic-electric loudness portion 816 to exhibit more or less curvature (see the "Q-Factor" arrows) on the curve 806. The Q-Factor may also be used to adjust the sections 818 and/or 820 as well. The output of this figure is in SPL units, which can be used for some implementations such as for acoustic or vibratory outputs. While the output is illustrated as being an SPL value (FIG. 8), in acoustic-to-electrical applications, for example, the output could alternatively be a current level (using T-Level and C-Level for TSPL and CSPL, respectively).

Figure 10:
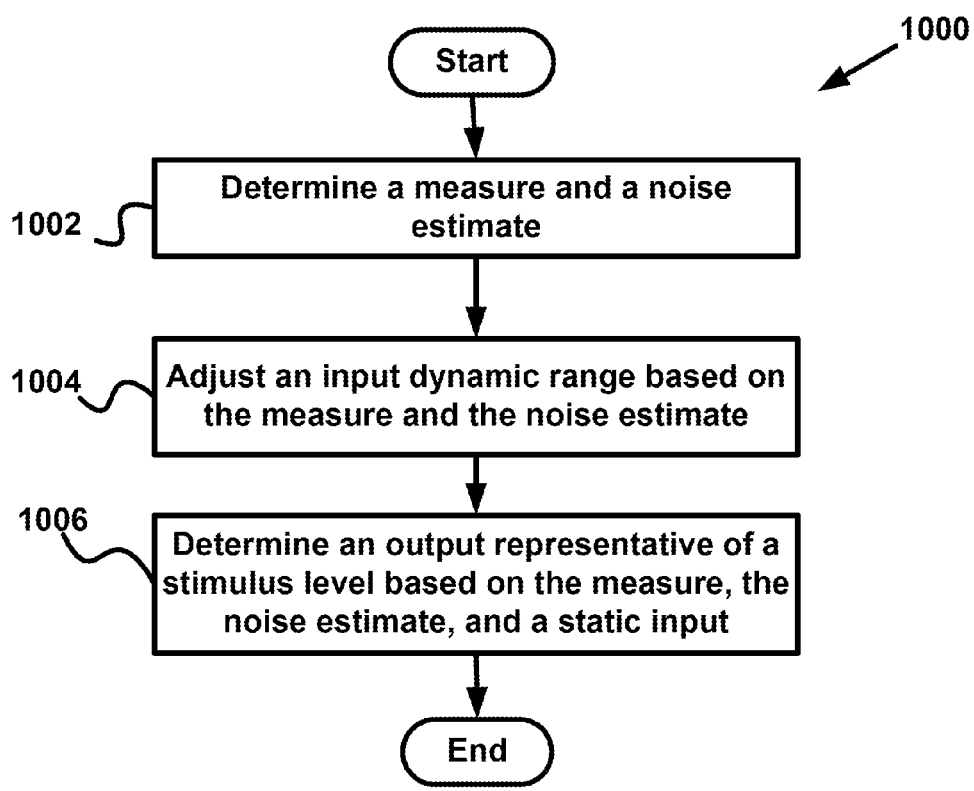
FIG. 10 is a flow diagram illustrating a method according to a second method.

FIG. 10 is a high-level flow diagram illustrating a method 1000 of processing an audio signal, according to one embodiment and as described in further detail above. A sound processor, such as the sound processor 208 illustrated in FIG. 2, and further described with respect to FIGS. 4 and 5, performs the steps of the method 1000. In block 1002, the method 1000 includes determining a measure and a noise estimate. The measure module 502 and noise estimate module 504 of the device 500 of FIG. 5 respectively determine the measure and noise estimate, according to one embodiment. In one example, the method 1000 includes determining the measure and/or the noise estimate for each of a plurality of frequency channels in the audio signal, such as described with respect to the spectral analysis 1 module 524 and spectral analysis 2 module 526 of FIG. 5.

In block 1004, the method 1000 includes adjusting an input dynamic range based on the measure and the noise estimate. In one example, the audio signal is an input audio signal composed of a plurality of samples, and the adjusting is performed for one of the plurality of samples. In a further example in which the audio signal has a plurality of frequency channels, the adjusting is performed for each channel in a channelized audio signal.

In block 1006, the method 1000 includes determining an output 1006 representative of a stimulus level, based on the measure, the noise estimate, and a static input, such as an asynchronously-received user input corresponding to volume or sensitivity (see user inputs 404 in FIG. 4), for example. Alternatively, the static input includes a device-specific parameter and a user-specific parameter (see static inputs 406 in FIG. 4), such as an MIN-SPL input, a MAX-SPL input, a T-Levels input, a C-Levels input, and/or a Q-Factor input. In the case where the audio signal is a channelized input audio signal, the method 1000 may include determining the output for each channel. In one example, determining the output may include determining a stimulus level according to one or more of a stimulus level, current level, a pulse width, a vibration rate, and an interphase gap.

The method 1000 may further include communicating the output to a stimulation device, such as the stimulation decoder 306 and stimulation component 308 illustrated in FIG. 3. In one example, the stimulation device includes a first subcomponent that generates the stimulus based on the output and sends the stimulus to a second component (e.g. an array of cochlear electrodes) that delivers the stimulus to the body part (e.g. a cochlea) of the user.

While much of the description above is in terms of a cochlear implant, the methods are applicable to other auditory devices that are not cochlear implants. For instance, if the auditory device is a bone conduction device, the implanted unit includes a transducer instead of the electrode array. In this example, the implanted unit uses the transducer to cause vibrations on the user skull capable of stimulating the user's cochlea. Similarly, for auditory devices other than hearing prostheses, there will likely be no implanted unit, and instead, a different type of stimulation device (e.g. speaker transducer or wearable vibratory device) will be used.

In the acoustic and vibratory context, as discussed above, non-linear mapping curves may be more appropriate. In addition, it may be desirable to limit the effective gain changes between neighboring channels (e.g. within about 6 dB of effective applied gain, produced by mapping, of each other). The primary difference, of course, will be in the type of stimulation provided (vibrating a speaker or motor rather than applying a stimulus signal to an electrode) and possibly in the domains used for calculating the fitting curve (loudness growth function). However, application to the acoustic or vibratory context still entails altering an input dynamic range during operation/use of an auditory device to help ensure that the most important part of an input audio signal is used for stimulation. At a high level, this is achieved by mapping an upper portion (e.g. a 95th percentile) of the input audio signal to an upper portion of the dynamic range and by mapping a noise level (e.g. a noise estimate) to a lower portion of the dynamic range.

The examples were illustrated in a unilateral cochlear implant system. However, some or all embodiments are also applicable to bilateral cochlear implant systems, as well as other systems incorporating more than a signal auditory device. In the case of bilateral auditory devices, each auditory device preferably includes a processing unit that communicates (via a wired or wireless connection) information pertaining to the microphone signal and the algorithmic state of the contralateral device (e.g. the left side device communicates its microphone signal and algorithmic state to the right side device, and vice versa).

A bilateral auditory device comprising a first processing unit associated with a first device (such as a left-side device) and a second processing unit associated with a second device (such as a right-side device) may be configured to perform a method for processing an audio signal according to variations of the methods described. For example, in one embodiment, the method includes the first processing unit determining an input dynamic range based, at least in part, on a communication received from and associated with the second processing unit. Such a communication could include a dynamic TSPL, a dynamic smoothed TSPL, a dynamic CSPL, a dynamic smoothed CSPL, a break rule output, a scaling value input, a volume input, a sensitivity input, and/or a Q-Value input associated with the second processing unit, for example. Upon determining the input dynamic range, the first processing unit could then determine an output representative of a stimulus level for the first device, based on the determined input dynamic range. In another embodiment, the first processing unit communicates the determined input dynamic range to the second processing unit. The second processing unit may, in turn, similarly utilize the communicated dynamic range or other communicated information in processing an audio signal.

Under such a bilateral auditory device system, the embodiments set forth herein preferably have access to the raw acoustic signal from both sides of the auditory devices (either external to the body or implanted). Alternatively, if communication bandwidth is limited between the two sides, the embodiments preferably have access to the algorithmic state of each side. For example, the two auditory devices may share information on the signal-to-noise (SNR) ratio of each side and the gain and threshold states of each respective side's processing.

Bilateral communications permit the algorithm to make informed decisions on mapping adjustments such that important cues employed in binaural hearing are preserved in real-world listening environments. Such preservation of binaural cues includes inter-aural level differences and binaural head shadow effects, thereby preserving the ability to localize the target information (e.g. a speaker's voice) and mask competing noises from the captured signals from each auditory device's microphones.

Bilateral communication also permits optimization and coordination of the front-end processing specific to the directionality of the microphones, not excluding the application of beamforming technologies. Here, the knowledge of each sides' acoustic signal and/or state allows for the adjustment of the directivity to best match the algorithm's binaural state, such that one side may serve as a noise reference (e.g. for use in determining a noise estimate) and the other side may provide target information content. A further benefit of this front-end optimization is the adjustment of gain and threshold to ensure that each side's respective loudness is matched in accordance with the current listening environment.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method of processing an audio signal at an auditory device, comprising:
    determining a measure and a noise estimate of the audio signal;
    adjusting, based on the measure and the noise estimate, at least an upper portion of an input dynamic range of the auditory device; and
    determining an output representative of a stimulus level based on the measure, the noise estimate, and a static input.

2. The method of claim 1, further comprising communicating the output to a stimulation device.

3. The method of claim 1, wherein the audio signal is an input signal composed of a plurality of samples, and wherein the adjusting is performed for one of the plurality of samples.

4. The method of claim 1, wherein determining the output includes applying at least one user input corresponding to volume or sensitivity.

5. The method of claim 4, further comprising asynchronously receiving the at least one user input.

6. The method of claim 1, wherein the static input includes at least one of device-specific parameter related to the specific auditory device and a user-specific parameter set by an audiologist during fitting of the auditory device to a user.

7. The method of claim 1, wherein the audio signal is separated into a plurality of frequency channels, and wherein the method further comprises:
    determining at least one of the measure and the noise estimate for an audio signal component in each of a plurality of frequency channels.

8. The method of claim 7, further comprising:
    adjusting at least an upper portion of an input dynamic range of the auditory device for each of the frequency channels based on the measure and noise estimate associated with the audio signal component in a respective frequency channel; and
    determining an output for each frequency channel.

9. The method of claim 1, further comprising adjusting an acoustic-to-electric mapping function based on the measure and the noise estimate, wherein determining the output includes applying the acoustic-to-electric mapping function to the audio signal.

10. The method of claim 1, wherein the static input includes a minimum sound pressure level, a maximum sound pressure level, a T-Level, and a C-Level, wherein the minimum sound pressure level corresponds to a noise floor, wherein the maximum sound pressure level corresponds to a maximum value of an analog-to-digital conversion, and wherein the T-Level and C-Level are, respectively, a minimum and a maximum of an electrical dynamic range of an acoustic-to-electric mapping function determined using at least one of the measure, the noise estimate, and the static input.

11. The method of claim 1, wherein the determining comprises calculating a gain and adjusting the audio signal based on the gain.

12. The method of claim 1, wherein the measure is a statistical measure of an upper amplitude of the audio signal over a preceding time period.

13. The method of claim 12, wherein the statistical measure is a percentile estimate.

14. The method of claim 1, wherein the measure is a measure of a characteristic of an average peak amplitude of the audio signal over the preceding time period.

15. The method of claim 1, wherein adjusting at least the upper portion of the input dynamic range based on the measure and the noise estimate comprises:
    mapping the upper portion of the audio signal as identified by a measure of an upper amplitude of the audio signal over the preceding time period to an input dynamic comfort sound pressure level (CSPL) parameter.

16. The method of claim 15, further comprising:
    setting an input dynamic threshold sound pressure level (TSPL) parameter.

17. The method of claim 16, further comprising performing at least one of the following determining and adjusting steps (a)-(f) prior to the determining an output representative of a stimulus level:
    (a) determining whether the input dynamic CSPL parameter is greater than an upper value maximum limit, and if so, adjusting the input dynamic CSPL parameter to no more than the upper value maximum limit;
    (b) determining whether the input dynamic CSPL parameter is less than an upper value minimum limit, and if so, adjusting the input dynamic CSPL parameter to no less than the upper value minimum limit;
    (c) determining whether the input dynamic TSPL parameter is greater than a lower value maximum limit, and if so, adjusting the input dynamic TSPL parameter to no more than the lower value maximum limit;
    (d) determining whether the input dynamic TSPL parameter is less than a lower value minimum limit, and if so, adjusting the input dynamic TSPL parameter to no less than the lower value minimum limit;

(e) determining whether a difference between the input dynamic CSPL parameter and the input dynamic TSPL parameter is greater than a maximum difference threshold, and if so, adjusting at least one of the input dynamic CSPL parameter and the input dynamic TSPL parameter so that the difference is not greater than the maximum difference threshold; and (f) determining whether the difference between the input dynamic CSPL parameter and the input dynamic TSPL parameter is less than a minimum difference threshold, and if so, adjusting at least one of the input dynamic CSPL parameter and the input dynamic TSPL parameter so that the difference is not less than the minimum difference threshold.

18. The method of claim 16, wherein setting the input dynamic TSPL parameter comprises:
determining a noise-level estimate during a noise smoothing time period; and
setting the input dynamic TSPL parameter to the noise-level estimate.

19. The method of claim 15, further comprising:
determining whether a magnitude of the audio signal exceeds the input dynamic CSPL parameter by a break threshold, and if so, increasing the input dynamic CSPL parameter.

20. The method of claim 1, wherein the determining an output representative of a stimulus level includes:
determining at least one of a signal amplitude, a pulse width, and an interphase gap for a stimulation signal.

21. An auditory device, comprising:
a processing unit configured to:
determine a measure of an upper amplitude of the audio signal over a preceding time period and a noise estimate of the audio signal for at least one of a plurality of samples of an audio signal; and
identify, based on the noise estimate and the measure, an input dynamic range for mapping the at least one of the plurality of samples of the audio signal to a corresponding stimulation signal.

22. The auditory device of claim 21, wherein the measure is a statistical measure of an upper bound of the at least one of the plurality of samples of the audio signal over the preceding time period.

23. The auditory device of claim 22, wherein the statistical measure is a percentile estimate.

24. The auditory device of claim 21, wherein the measure is a measure of a characteristic of an average peak amplitude of the audio signal over the preceding time period.

25. The auditory device of claim 21, wherein to identify the input dynamic range for mapping the at least one of the plurality of samples of the audio signal to a corresponding stimulation signal, the processing unit is configured to map an upper portion of the at least one of the plurality of samples of the audio signal as identified by the measure to an input dynamic comfort sound pressure level (CSPL) parameter.

26. The auditory device of claim 21, wherein to identify, based on the noise estimate and the measure, an input dynamic range for mapping the at least one of the plurality of samples of the audio signal to a corresponding stimulation signal, the processor is configured to:
adjust, based on at least the measure, at least an upper portion of the input dynamic range.

27. The auditory device of claim 21, the device further comprising:
a stimulation unit for providing a stimulus generated based on the stimulation signal to a user of the auditory device, wherein the stimulus comprises one or more of an electrical stimulus and a mechanical stimulus.

28. The auditory device of claim 21, wherein the processing unit is further configurable to determine respective noise estimates and measures for other of the plurality of samples and to temporally smooth a plurality of the noise estimates and a plurality of the measures while identifying the input dynamic range.

29. The auditory device of claim 21, wherein the processing unit is further configurable to determine respective noise estimates and measures for other of the plurality of samples, to identify a plurality of input dynamic ranges based on the determined respective noise estimates and measures, and to temporally smooth the identified plurality of input dynamic ranges for mapping the audio signal to a corresponding stimulation signal.

30. The auditory device of claim 21, wherein the processing unit is configured to apply at least one rule that uses at least one of the noise estimate and the measure to identify the input dynamic range, and wherein the at least one rule comprises at least one of an information rule and a noise rule,
wherein the information rule comprises determining at least one of whether an upper value of the input dynamic range is greater than an upper value maximum limit and whether the upper value of the input dynamic range is less than an upper value minimum limit, and, upon determining that the upper value of the input dynamic range is greater than the upper value maximum limit or less than the upper value minimum limit, adjusting the upper value respectively to the upper value maximum limit or the upper value minimum limit, and
wherein the noise rule comprises determining at least one of whether a lower value of the input dynamic range is less than a lower value minimum limit and whether the lower value of the input dynamic range is greater than a lower value maximum limit, and, upon determining that the lower value of the input dynamic range is less than the lower value minimum limit or greater than the lower value maximum limit, adjusting the lower value respectively to the lower value minimum limit or the lower value maximum limit.

31. The auditory device of claim 21, wherein the processing unit is configured to apply at least one rule that uses at least one of the noise estimate and the measure to identify the input dynamic range, and wherein the at least one rule comprises at least one of a stretch rule and a squash rule,
wherein the stretch rule comprises determining whether a difference between an upper value of the input dynamic range and a lower value of the input dynamic range is greater than a maximum difference threshold, and if so, adjusting at least one of the upper value and the lower value so that the difference is not greater than the maximum difference threshold, and
wherein the squash rule comprises determining whether the difference between the upper value and the lower value is less than a minimum difference threshold, and if so, adjusting at least one of the upper value and the lower value so that the difference is not less than the minimum difference threshold.

32. The auditory device of claim 21, further comprising at least one user input to set at least one of a volume and a sensitivity, wherein the volume is used in identifying an upper value of at least one of the input dynamic range and an output dynamic range, and wherein the sensitivity is used in identifying a lower value of at least one of the input dynamic range and the output dynamic range.

33. The auditory device of claim 21, wherein the processing unit is further configurable to map the audio signal to the corresponding stimulation signal according to a map using a lower value of the input dynamic range and an upper value of the input dynamic range, wherein the input dynamic range maps to a corresponding output range predetermined for the user and the stimulation device.

34. The auditory device of claim 21, wherein the at least one rule comprises a break rule comprising determining whether a magnitude of the audio signal exceeds an upper value of the input dynamic range by a break threshold, and if so, increasing the upper value of the input dynamic range.

\* \* \* \* \*